(12) United States Patent
Arinaga et al.

(10) Patent No.: US 8,309,365 B2
(45) Date of Patent: Nov. 13, 2012

(54) METHOD FOR EVALUATING TARGET MOLECULES

(75) Inventors: Kenji Arinaga, Garching (DE); Ulrich Rant, Garching (DE); Erika Pringsheim, Garching (DE); Wolfgang Kaiser, Garching (DE); Jelena Knezevic, Garching (DE)

(73) Assignees: Fujitsu Limited, Kawasaki (JP); Technical University of Munich, Garching (DE)

( * ) Notice: Subject to any disclaimer, the term of this patent is extended or adjusted under 35 U.S.C. 154(b) by 123 days.

(21) Appl. No.: 12/626,729

(22) Filed: Nov. 27, 2009

(65) Prior Publication Data

US 2010/0133121 A1     Jun. 3, 2010

(30) Foreign Application Priority Data

Nov. 28, 2008   (JP) ................. 2008-303621

(51) Int. Cl.
   *G01N 21/76* (2006.01)
   *G12Q 1/00* (2006.01)
(52) U.S. Cl. .......... 436/172; 436/86; 436/149; 324/600; 324/605; 324/71.1; 205/777.5
(58) Field of Classification Search .................. 436/172, 436/86, 149; 324/600, 605, 71.1; 205/777.5
   See application file for complete search history.

(56) References Cited

U.S. PATENT DOCUMENTS

| 7,169,617 B2 | 1/2007 | Arinaga et al. |
| 2005/0069932 A1* | 3/2005 | Arinaga et al. .............. 435/6 |
| 2006/0003437 A1 | 1/2006 | Fujihara et al. |

FOREIGN PATENT DOCUMENTS

| JP | 2004-28798 A | 1/2004 |
| JP | 2005-283560 A | 10/2005 |
| JP | 2006-58094 A | 3/2006 |

OTHER PUBLICATIONS

Drummond, T. Gregory et al.; "Electrochemical DNA sensors"; Nature Biotechnology, Oct. 2003, pp. 1192-1199, vol. 21, No. 10.
Wang, Joseph; "Survey and Summary From DNA biosensors to gene chips"; Nucleic Acids Research, 2000, pp. 3011-3016, vol. 28, No. 16.
Ulman, Abraham; "Formation and Structure of Self-Assembled Monolayers"; Chem. Rev., 1996, pp. 1533-1554, vol. 96, No. 4.
Rant, Ulrich et al.; "Dissimilar Kinetic Behavior of Electrically Manipulated Single- and Double-Stranded DNA Tethered to a Gold Surface"; Biophysical Journal, May 2006, pp. 3666-3671, vol. 90.

(Continued)

*Primary Examiner* — Jill Warden
*Assistant Examiner* — Monique Cole
(74) *Attorney, Agent, or Firm* — Westerman, Hattori, Daniels & Adrian, LLP

(57) ABSTRACT

A method for evaluating a target molecule bound to a probe molecule provided with a marker includes: applying AC voltage between a working electrode provided on a substrate and a counter electrode; and using a signal obtained from the marker on the probe molecule bound to the working electrode when a frequency of the AC voltage is varied, or an average value of the signal, to determine at least one of a Stokes radius or molecular weight of the target molecule, a binding rate between the probe molecule and the target molecule, a binding rate constant therebetween, a dissociation rate therebetween, and a dissociation rate constant therebetween.

28 Claims, 16 Drawing Sheets

OTHER PUBLICATIONS

Rant, Ulrich et al.; "Dynamic Electrical Switching of DNA Layers on a Metal Surface"; Nano Letters, 2004, pp. 2441-2445, vol. 4, No. 12.

Sendner C. et al.; "Dynamics of end grafted DNA molecules and possible biosensor applications" Physica Status Solidi (A) Applications and Materials Nov. 2006 Wiley-Vch Verlag DE, vol. 203, No. 14 Nov. 10, 2006 pp. 3476-3491.

Extended European Search Report dated Mar. 17, 2010, issued in corresponding European Patent Application No. 09177413.

Rant, Ulrich et al. "Switchable DNA Interfaces for the Highly Sensitive Detection of Label-Free DNA Targets." Proceedings of the National Academy of Sciences, vol. 104, No. 44, pp. 17364-17369. Oct. 30, 2007.

* cited by examiner

Fluorescent dye Cy3

Methylene blue

Ferrocene

Digoxigenin

METHOD FOR EVALUATING TARGET MOLECULES

CROSS-REFERENCE TO RELATED APPLICATIONS

This application is based upon and claims the benefit of priority from the prior Japanese Patent Application No. 2008-303621, filed on Nov. 28, 2008, the entire contents of which are incorporated herein by reference.

TECHNICAL FIELD

The present invention relates to methods for evaluating targets (target molecules), which methods are intended for use in biochips such as DNA chips and protein chips.

BACKGROUND

In recent years, nanotechnology, often alluded to by use of the term 'nano', has attracted a great deal of interest.

Within the realm of nanotechnology, research and development is especially active in nanobiotechnology, a new field combining semiconductor nanotechnology and biotechnology with the potential to achieve fundamental solutions to existing problems.

In this field of nanobiotechnology, particular attention has been focused on biochips, such as DNA chips (or DNA microarrays) and protein chips, as an effective means of for simplifying nucleic acid and protein testing in such areas as clinical diagnosis and drug therapy which is particularly effective in gene analysis. Biochips are substrates formed of glass, silicon, plastic, metal or the like on which multiple differing analytes composed of bio-molecules such as DNA and proteins are placed as spots in high-density arrays (see T. G. Drummond et al.: "Electrochemical DNA sensors," *Nature Biotech.* 21, No. 10, 1192-1199 (2003); and J. Wang: "Survey and Summary from DNA biosensors to gene chips," *Nucleic Acids Research* 28, No. 16, 3011-3016 (2000)).

In recent years, devices known as MEMS and μTAS, which are manufactured based on technology for evaluating very small targets by combining micromachining technology and microsensing technology, with a functional surface (evaluation part) formed on some portion of a solid substrate by binding functional molecules, or molecules bound to functional molecules onto to the solid substrate, have drawn attention as devices which provide great improvements in evaluation sensitivity and evaluation time. "MEMS" is an abbreviation for Micro Electro Mechanical Systems, and refers to a technology for manufacturing very small devices based on semiconductor technology, or to precision micromachines manufactured using such technology; the term generally refers to systems in which a plurality of functional components—mechanical, optical, fluidic, etc.—have been integrated and miniaturized. "μTAS" is an abbreviation for Micro Total Analysis System, and refers to a chemical analysis system created by miniaturizing, arraying and integrating micropumps, microvalves, sensors and the like. These devices generally have a functional surface composed of functional molecules with specific functions, or molecules bound to such functional molecules, often fixed (bound) in a self-assembling manner on a substrate. Many methods for electrically or optically evaluating reactions at the functional surface are used in these devices.

Among these methods, optical evaluation methods are methods in which a target to be evaluated is modified with an optical label such as a fluorescent dye, and the target is quantitatively evaluated based on the optical intensity. Owing to their high sensitivity, such methods are widely used in DNA chips.

However, because a procedure that involves modifying the target with a label is essential to such methods, cumbersome steps such as labeling and rinsing are required. Other problems include mis-detection due to contamination by the unattached (unreacted) label, and the evaluation of targets which attach non-specifically to the evaluation part rather than binding specifically with the probe.

Accordingly, there exists a desire for the development of highly selective, low-noise methods of evaluation which do not require the target to be modified with a label (non-label techniques) and which avoid the mis-detection of non-specifically adsorbed target.

One known technique for evaluating label-free target molecules is a method in which a marker is modified into a charged probe molecule, the probe molecule is fixed to an electrode and driven by an electrical field, and the drive state is monitored by signals from the marker. When a target molecule binds specifically with the probe molecule, the drive state of the probe changes, which change is evaluated by the marker that has been modified into a probe (see U. Rant et al.: "Dynamic electrical switching of DNA layers on a metal surface," *Nano Lett.* 4, No. 12, 2441-2445 (2004); claims of Japanese Patent Application No. 2004-238696; claims of Published U.S. Patent Application No. 2005/069932). The principle underlying this technique is to monitor changes in the signals from the marker that arise due to the changes in the distance between the marker attached to the end of the probe molecule and the substrate as the electrically charged probe molecule is attracted to or repelled by the electric field. So long as the driving frequency is in a frequency range (up to about 1 MHz) that allows formation of an electric double layer as the source of the electric field, evaluation of the target molecule is possible by monitoring signals from the marker that are synchronous with the driving potential.

SUMMARY

According to one aspect disclosed in this specification, the invention provides a method for evaluating a target molecule bound to a probe molecule provided with a marker, which method includes applying AC voltage between a working electrode provided on a substrate and a counter electrode; and using an average value of the signal or a frequency response of the signal obtained from the marker on the probe molecule bound to the working electrode when a frequency of the AC voltage is varied to determine a Stokes radius or molecular weight of the target molecule.

According to another aspect disclosed in the specification, the invention provides a method for evaluating a target molecule bound to a probe molecule provided with a marker, which method includes applying AC voltage between a working electrode provided on a substrate and a counter electrode; and using an average value of the signal or a frequency response of the signal obtained from the marker on the probe molecule bound to the working electrode when a frequency of the AC voltage is varied to determine at least one from the following: a binding rate between the probe molecule and the target molecule, a binding rate constant therebetween, a dissociation rate between the probe molecule and the target molecule, and a dissociation rate constant therebetween.

The various aspects of the invention disclosed in this specification achieve novel methods for evaluating target molecules at a high selectivity and low noise. That is, evaluation methods are achieved which do not require marker modification of the target molecule, which prevent the residual presence of evaluation marker when such marker is used to modify the target molecules from adversely affecting evaluation, and which prevent the mis-detection of nonspecifically adsorbed target.

DESCRIPTION OF THE EMBODIMENTS

Figure 1A:
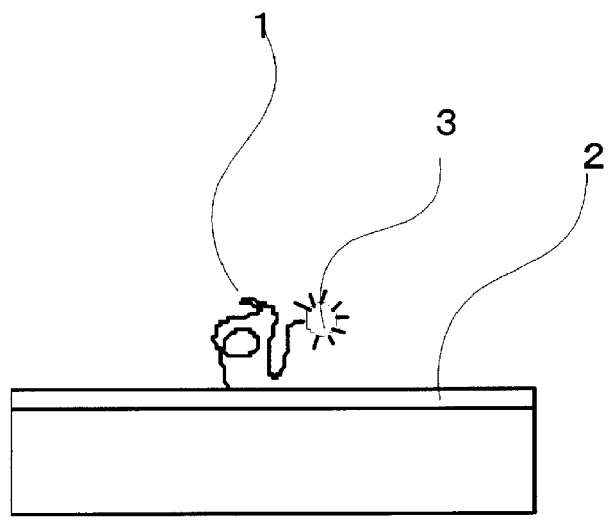
FIG. 1A is a schematic view showing the behavior of a probe molecule.

Various embodiments of the invention are described below in conjunction with the accompanying diagrams and working examples. These diagrams and examples and the description are given for the purpose of illustrating the invention and are not intended to limit the scope of the invention. It is to be understood that other embodiments may fall within the scope of the present invention insofar as they are in keeping with the spirit of the invention as set forth in the appended claims.

In the method for evaluating target molecules disclosed in this specification, target molecules bound to probe molecules are evaluated by applying AC voltage between a working electrode provided a and a counter electrode; and observing signals obtained from markers modified on the probe molecules bound to the working electrode. The signal behavior of the markers in response to changes in the frequency of the AC voltage is observed at this time. The frequency of this AC voltage is called the driving frequency because it elicits movements of the probe molecules (e.g., stretching/contraction movements) that serve as the basis of the signal behavior of the markers. Eliciting such movements by the probe molecules is sometimes referred to as "driving" the probe molecules.

A method for evaluating target molecules bound to probe molecules by applying AC voltage between a working electrode provided on a substrate and a counter electrode, and observing the signals obtained from markers on probe molecules bound to the working electrode is disclosed in, for example, the claims of Japanese Patent Application Laid-open No. 2005-283560.

This method enables the novel evaluation of a target molecule at a high selectivity and low noise. Specifically, a method of evaluation is achieved which does not require the target molecule to be modified with a marker and which is able to prevent both the residual presence of any portion of an evaluation marker used to modify the target molecules from adversely affecting evaluation, and the mis-detection of nonspecifically adsorbed target molecules.

These low-noise molecular evaluation methods and evaluation devices are highly useful in the field of nanobiotechnology, and make it possible to furnish evaluation methods suitable for biochips such as DNA chips and protein chips, as well as evaluation devices which use such methods.

As used herein, "evaluation" means to detect whether or not a probe molecule or target molecule is present, to detect disparities and to quantify, and to determine physical values such as the Stokes radius, and the binding rate, binding rate constant, dissociation rate and dissociation rate constant between probe molecules and target molecules.

Target Molecule Evaluation Device

The foregoing method for evaluating target molecules is able to carry out evaluation by using a target molecule evaluating device which includes a working electrode on a substrate, a counter electrode, probe molecules which are bound to the working electrode, provided with a marker and capable of binding with a target molecule, means for applying a voltage between the working electrode and the counter electrode, and means for detecting signals from the markers. In cases where the signal detecting means is a fluorescence detecting means, the device may include an auxiliary means, such as a light irradiating means for causing the emission and quenching of fluorescence. The working electrode and counter electrode are used while immersed in an aqueous solution.

The following description pertains mainly to cases in which the emission and quenching of marker fluorescence is observed. However, as explained later in the specification, the signals are not limited only to fluorescence.

In the foregoing device, the probe molecules are made to be bound to the working electrode and the markers are placed on the probe molecules, then a voltage is applied, causing light emission or quenching of the markers by a quenching effect. The target molecules bound to the probe molecule can be evaluated by observing such emission/quenching behavior.

Emission/quenching of the marker is thought to be made possible by changes in the distance between the marker and the working electrode. The marker emits when it moves away from the working electrode, and quenches when approaches or comes into contact with the working electrode. Such movement by the marker is thought to be possible because of the ability of the probe molecules to be positively or negatively charged. For example, when the probe molecule is negatively charged, giving the working electrode a negative potential will cause the marker to move away from the working electrode, and giving the working electrode a positive potential will cause the marker to move toward the working electrode.

Figure 1B:
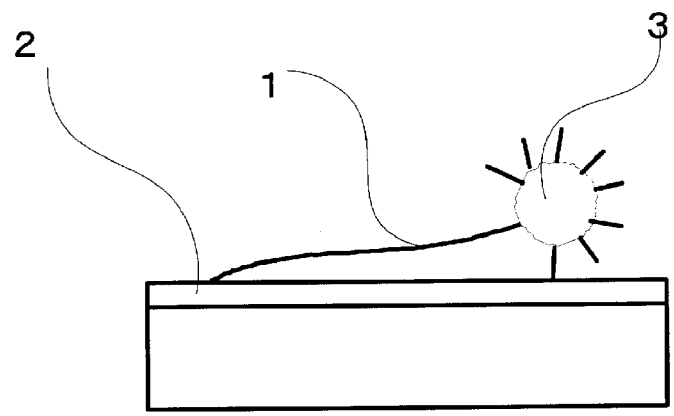
FIG. 1B is a schematic view showing the behavior of a probe molecule.
Figure 1C:
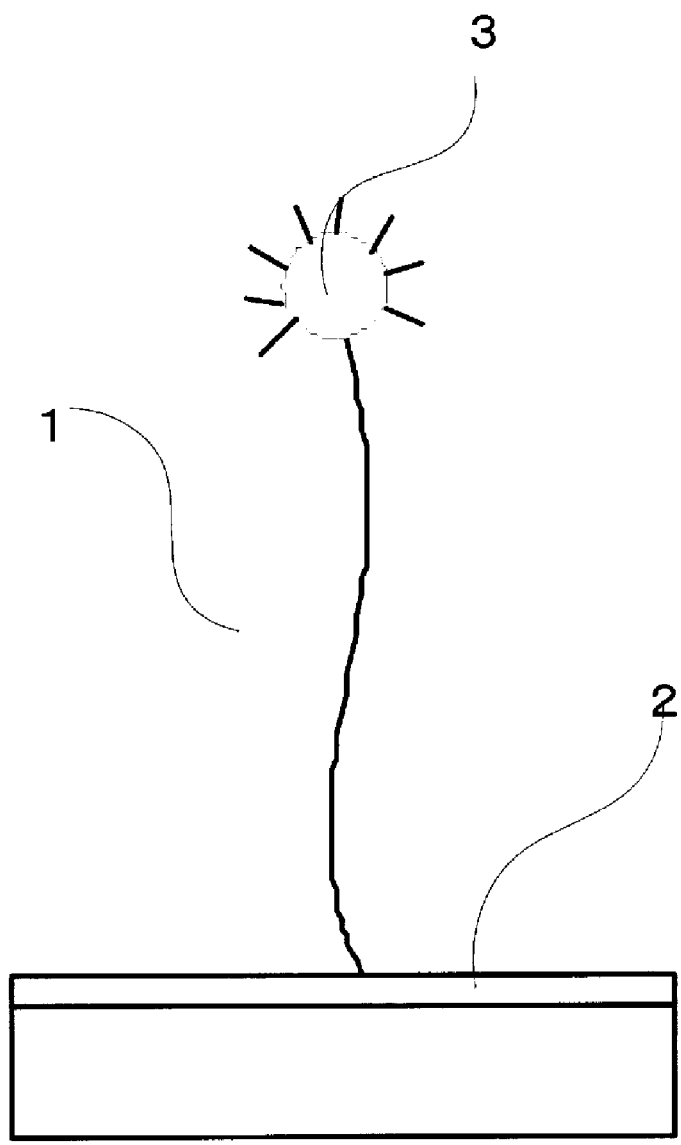
FIG. 1C is a schematic view showing the behavior of a probe molecule.

Such behavior is shown schematically in FIGS. 1A to 1C. FIG. 1A is a schematic diagram showing a probe molecule 1 which is bound to a working electrode 2 and in a contracted state, FIG. 1B is a schematic diagram showing a probe molecule 1 which is bound to a working electrode 2 and in a horizontally "toppled" state, and FIG. 1C is a schematic diagram showing a probe molecule 1 in a state that extends out from a working electrode 2. In FIGS. 1A and 1B, the marker 3 is either close to or in contact with the working electrode 2, whereas in FIG. 1C, the marker 3 is at a distance from the working electrode 2. This is the behavior that is thought to arise. In describing the stretching/contracting of the probe molecule in the present specification, the term 'stretching/contracting' is intended to refer to behavior like that shown in FIGS. 1A to 1C, although any behavior involving a change in the distance between the marker and the working electrode can be understood as "stretching/contracting." Accordingly, "stretching/contracting" is not limited only to the above-mentioned behavior.

Target Molecule

The target molecule is preferably one selected from, or includes one selected from, the group consisting of proteins, DNA, RNA, antibodies, natural or artificial single-stranded nucleotides, natural or artificial double-stranded nucleotides, aptamers, products obtained by the limited digestion of an antibody with a protease, organic compounds having affinity to proteins, biopolymers having affinity to proteins, complexes thereof and combinations of any of these. Positively or negatively charged ionic polymers may be included. Examples of the above complexes include complexes of the above substances with other substances, such as complexes of DNA with a negatively charged polymer. In addition to the above, further examples of the target molecule include plasma proteins, tumor markers, apoproteins, viruses, autoantibodies, coagulating and fibrinolytic factors, hormones, drugs in blood, nucleic acids, HLA antigens, lipoproteins, glycoproteins, polypeptides, lipids, polysaccharides and lipopolysaccharides.

As used herein, "nucleotide" refers to any one selected from the group consisting of mononucleotides, oligonucleotides and polynucleotides, and mixtures thereof. Such substances are often negatively charged. Use may be made of a single-stranded or double-stranded nucleotides. Moreover, it is possible for protein, DNA and nucleotides to be intermingled. Biopolymers include not only those originating from living organisms, but also those modified from biopolymers originating from living organisms, and synthesized molecules.

As used herein, "product" refers to a substance obtained by the limited digestion of an antibody with a protease and, to the extent that it accords with the gist of the embodiments disclosed in this specification, may include also the Fab fragment or (Fab)$_2$ fragment of an antibody, fragments originating from the Fab fragment or (Fab)$_2$ fragment of an antibody, and derivatives thereof.

Examples of antibodies that may be used include monoclonal immunoglobulin IgG antibodies. Examples of fragments originating from IgG antibodies that may be used include Fab fragments or (Fab)$_2$ fragments of IgG antibodies. In addition, use may also be made of fragments originating from such Fab fragments or (Fab)$_2$ fragments. Examples of organic compounds having affinity to proteins that may be used include enzyme substrate analogs such as nicotinamide adenine dinucleotide (NAD), enzyme activity inhibitors and neurotransmission inhibitors (antagonists). Examples of biopolymers having affinity to proteins include proteins that serve as substrates or catalysts for proteins, and constituent proteins in a molecular complexes.

Probe Molecule

The probe molecule may be any suitable molecule, so long as it is capable of binding to the working electrode and accords with the gist of the invention as disclosed in the present specification. However, a probe molecule which has a marker prior to binding of the target molecule is preferred.

It is preferable for the probe molecule to have the property of binding specifically to a target molecule. By having the property of binding specifically, a precise, highly selective, low-noise evaluation of the target molecule becomes easier. The type of bond and the binding part are not subject to any particular limitation, although it is preferable to avoid bonds having especially weak bond strengths.

The probe molecule generally has the function of changing the distance between the marker and the working electrode upon the application of AC voltage. As explained above, in order to give rise to a change in the distance between the marker and the working electrode with the application of an AC voltage, it is preferable for the probe molecule to be able to positively or negatively charge. Such a probe molecule is sometimes called a chargeable probe molecule.

The shape of the probe molecule is not subject to any particular limitation, and may be suitably selected according to the intended object. Examples of suitable shapes include linear, granular, and plate-like shapes, as well as combinations of two or more thereof. Of these, a linear shape is preferred.

The type of such a probe molecule is not subject to any particular limitation, and may be suitably selected according to the intended object. For example, biomolecules are suitable from the standpoint of use in the treatment and diagnosis of diseases. Specifically, at least one substance selected from the group consisting of proteins, DNA, RNA, antibodies, natural or artificial single-stranded nucleotides, natural or artificial double-stranded nucleotides, aptamers, products obtained by the limited digestion of an antibody with a protease, organic compounds having affinity to proteins, biopolymers having affinity to proteins, complexes thereof, positively or negatively charged ionic polymers, and combinations thereof is preferred because these substances are often easy to stretch/contract and often easily bind specifically as the probe molecule with a target molecule.

Preferred examples of positively charged ionic polymers include DNA which has been positively charged using guanidino group bonds on the main chain (guanidine DNA), and polyamines. Preferred examples of negatively charged ionic polymers include negatively charged natural nucleotides, polynucleotides and polyphosphoric acids. These molecules may be used singly, or as combinations of two or more types thereof.

The terms such as "nucleotide," "product," "antibody," "organic compounds having affinity to proteins," "biopolymers having affinity to proteins" used here have the same meanings as indicated above.

A natural nucleotide or an artificial nucleotide may be used as the probe molecule. Artificial nucleotides include both nucleotides which are completely artificial and nucleotides which are derived from natural nucleotides. Using an artificial nucleotide may be advantageous in some cases by enabling, for example, the detection sensitivity to be increased or the stability to be enhanced.

The nucleotide may be a single-stranded nucleotide, or may be a double-stranded nucleotide that is a pair of single-stranded nucleotides having a mutually complementary relationship. A single-stranded nucleotide is often preferable for ease of extension and contraction, whereas a double-stranded nucleotide is often preferable for lying down or standing up on the working electrode. It is also possible to use differing nucleotides on each electrode. The nucleotide chain should have a length of at least one residue. That is, mononucleotide chains are also acceptable.

Alternatively, a monoclonal antibody or a product obtained by limited degradation with a protease may be used as the probe molecule. Such molecules are useful because bonds that arise due to reactions similar to antigen-antibody reactions may be utilized, and because they function as probe molecules which bond specifically with the target molecule.

Preferred use may also be made of monoclonal antibodies, the Fab fragment or $(Fab)_2$ fragment of monoclonal antibodies, or fragments originating from the Fab fragment or $(Fab)_2$ fragment of monoclonal antibodies as the probe molecule. Here, "fragments originating from the Fab fragment or $(Fab)_2$ fragment of monoclonal antibodies" refers to, for example, a fragment obtained by segmentation of the Fab fragment or $(Fab)_2$ fragment of a monoclonal antibody or a derivative of the fragment thus obtained.

It is more preferable to use as the probe molecule an IgG antibody, the Fab fragment or $(Fab)_2$ fragment of an IgG antibody, or a fragment originating from an IgG antibody, or the Fab fragment or $(Fab)_2$ fragment of an IgG antibody. Here, "a fragment originating from the Fab fragment or $(Fab)_2$ fragment of an IgG antibody" refers to a fragment obtained by segmentation of the Fab fragment or $(Fab)_2$ fragment of an IgG antibody or a derivative of the fragment thus obtained. It is also preferable for the probe molecule to be an aptamer. Generally, probe molecules having a smaller molecular weight will have a better detection sensitivity, which is the reason why these are preferred.

In terms of the ease of binding with the working electrode, it is preferable for the probe molecule to be a polynucleotide having a thiol group (—SH) or a disulfide bond (—S—S—), or to include a polynucleotide having a thiol group (—SH) or a disulfide bond (—S—S—). DNA, RNA and complexes thereof with protein which have a thiol group (—SH) or a disulfide bond (—S—S—) at the end are especially preferred. The DNA and RNA may be single-stranded or double-stranded.

The size and length of the probe molecule are not subject to any particular limitation, and may be suitably selected according to the intended purpose. However, when the probe molecule is a polynucleotide, it is preferable for the polynucleotide to have at least six bases.

Electrode

The working electrode may be any suitable electrode which is capable of binding with the probe molecule, and for which the signals obtained from markers on the probe molecules bound to the working electrode are capable of changing in response to AC voltage applied between the working electrode and a counter electrode, so long as it accords with the gist of the embodiments disclosed in the present specification. Nor is the working electrode subject to any particular limitation with regard to shape. Any bond in accordance with the gist of the embodiments disclosed in the present specification may be used as the bond in this case. Illustrative examples include not only chemical bonds such as covalent bonds and coordination bonds, but also biological bonds, electrostatic bonds, physical adsorption, and chemical adsorption. From the standpoint of the stability of probe molecule movement in response to an external electric field, a chemical bond is preferred. Of chemical bonds, a bond containing a sulfur atom (S) is preferable in terms of the ease and controllability of binding. Preferred examples include bonds between sulfur and the working electrode which use a thiol group (—SH) or a disulfide bond (—S—S—).

For example, a working electrode may be arrived at by providing an electrode on the substrate surface, and providing on the electrode surface a structural portion (probe molecule-binding part) to which the probe molecule is capable of binding. The working electrode may have a single-layer or multilayer structure, or may have a structure other than one that is layered.

The material making up the substrate in this case is not subject to any particular limitation. Preferred examples include glass (e.g., quartz glass), ceramic, plastic, metal, silicon, silicon oxide, silicon nitride, and sapphire. These materials may be used singly as one type or as a combination of two or more types.

The shape, structure, size, surface condition and number of the electrodes are not subject to any particular limitation, and may be suitably selected according to the intended use. The shape may be, for example, tabular, circular or elliptical. The surface condition may be, for example, a glossy surface or a rough surface. The size may be suitably selected according to the intended use without any particular limitation.

The surface of the electrodes may be covered with a dielectric film so as to leave only a portion of the electrodes exposed, and the size, shape and other attributes of the electrodes may be adjusted to an extent that is appropriate and desirable. The number of substrates, which is not subject to any particular limitation and can be selected as appropriate for the intended use, may be one or may be two or more.

The dielectric film is not subject to any particular limitation concerning the material, shape, structure, thickness and size thereof, and may be suitably selected according to the intended use from among known dielectric films. The material making up the dielectric film is exemplified by a resist material. Examples of suitable resist materials include g-line resists, i-line resists, KrF resists, ArF resists, $F_2$ resists and e-beam resists.

The material making up the electrodes is not subject to any particular limitation, and may be selected as appropriate for the intended object. Exemplary materials include metals, alloys, conductive resins, and carbon compounds. Illustrative examples of metals include gold, platinum, silver, copper and zinc. Illustrative examples of alloys include alloys of two or more of the above-mentioned metals. Illustrative examples of conductive resins include polyacetylene, polythiophene, polypyrrole, poly(p-phenylene), polyphenylene vinylene, and polyaniline. Illustrative examples of carbon compounds include conductive carbon and conductive diamond. Any of the above may be used singly or as combinations of two or more. Noble metals such as gold are chemically stable and are thus preferred for use, the reason being that, when a biopolymer is used as the probe molecule, immobilization of the probe molecule on the working electrode can easily be carried out. A plurality of working electrodes may be provided on the substrate.

Figure 2:
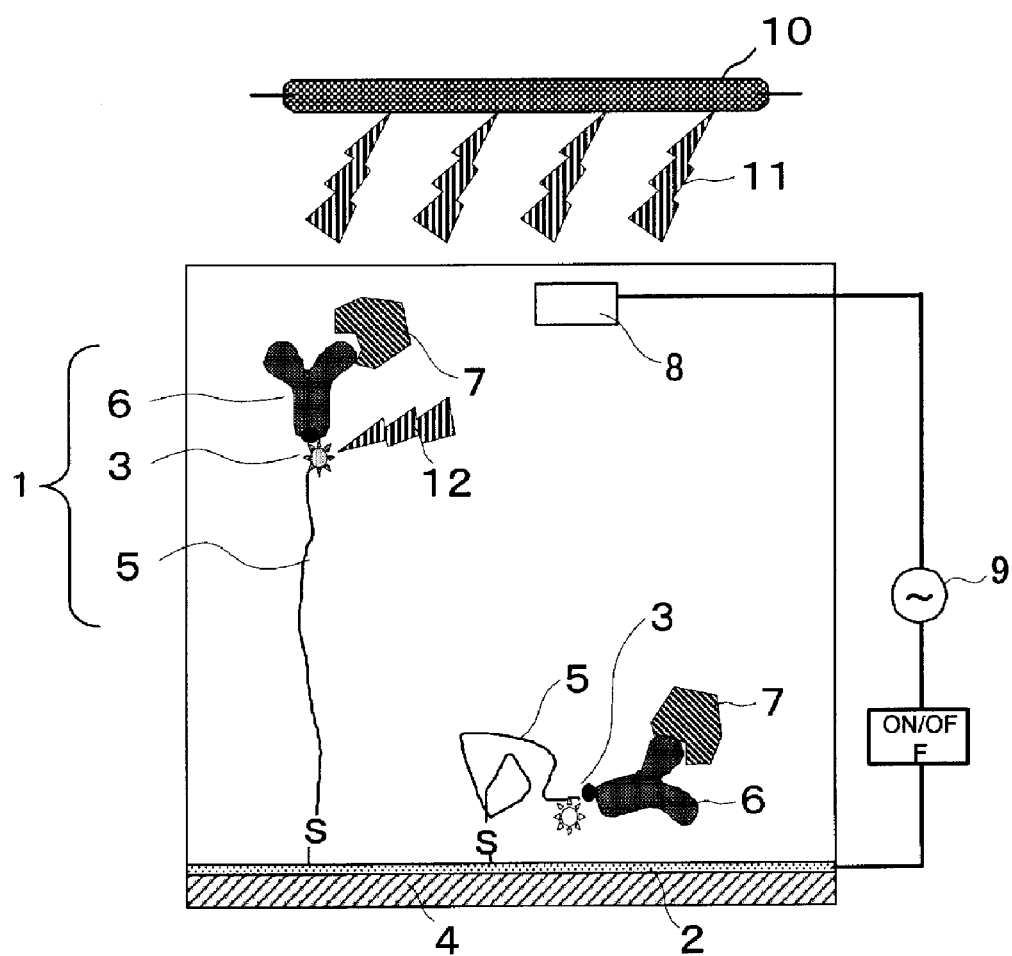
FIG. 2 is a schematic view of the target molecule evaluating device used in Example 3, and shows the behavior at various parts on a probe molecule.

When binding with the probe molecules is possible without a particular probe molecule binding part, no probe molecule binding part need be provided on the probe molecules. This is illustrated by cases in which the probe molecule is a nucleotide and binds directly to a gold layer via a thiol group thereon. An example is shown in FIG. 2 where, by reacting the probe molecule for 24 hours at room temperature with a polished gold electrode, a probe molecule 1 provided with a marker 3, a responsive portion 5 having a natural single-stranded oligonucleotide structure and a target molecule binding part 6 (portion composed of the marker 3, responsive portion 5 and target molecule binding part 6) is bound with a target molecule 7 on a gold electrode (working electrode 2) provided on a sapphire substrate 4. The responsive portion 5 refers here to a portion which has a stretching/contracting function, and the target molecule binding part 6 refers to a portion which binds with the target molecule to be evaluated. If the target molecule binding part 6 has a function to bind specifically with the target molecule, the probe molecule and the target molecule 7 will bind specifically. The "S" at the bottom of the single-stranded oligonucleotide structure indicates that the probe molecule binds directly with the gold electrode 2 via a thiol group. Known metals other than gold may be used as the electrode surface which bonds with the thiol group. In FIG. 2, a monoclonal immunoglobulin IgG is fixed, as the target molecule-binding part 6 having the characteristic of binding specifically to the target molecule 7, to the end of an oligonucleotide chain.

The left side of FIG. 2 shows the probe molecule 1 in an extended state, and the right side shows the probe molecule 1 in a contracted state. The probe molecule 1 in a contracted state can be rendered into an extended state by applying a specific potential difference between the gold electrode 2 and a counter electrode 8 with an external electric field applying apparatus 9.

If light 11 is irradiated at this time from a light irradiating device 10, fluorescence 12 will be obtained. In FIG. 2, the object of evaluation is a target molecule bound to the probe molecule. When the object of evaluation is the probe molecule itself (i.e., the probe molecule alone, prior to binding with a target molecule), fluorescence emission/quenching is evaluated without binding a target molecule to the probe molecule.

In FIG. 2, a thiol group and a marker have been introduced into the single-stranded oligonucleotide beforehand. It is desirable to introduce the thiol group and the marker at the end of the single strand. If the thiol group has been introduced at the 5' end, it is preferable to introduce the marker at the 3' end, and vice versa. In this example, the oligonucleotide chain was fixed onto a circular gold electrode having a diameter of 1 mm.

When a probe molecule binding part is provided as part of the probe molecule, it may be made of any material capable of binding with the probe molecule, such as molecules capable of binding to the probe molecule via chemical bonds or intermolecular forces. Once the probe molecule binding part has bound with the probe molecule, the portion composed of the probe molecule binding part and the probe molecule may be thought of as a probe molecule. If the probe molecule binding part is capable of stretching/contracting, the probe molecule prior to binding with the probe molecule binding part need not have a stretching/contracting ability.

It is generally ideal for binding between the working electrode and the probe molecule to be quantitative. However, some bonds may have quite a high dissociation rate constant. If the dissociation rate constant is too high, during rinsing in a buffer solution, for example, the bonds will gradually decrease. In this sense, it is generally preferable for the dissociation rate constant in bonds between the working electrode and the probe molecule to be $10^{-5}$ or less.

When such a working electrode is immersed in an aqueous solution as the medium and an AC electric field is applied between the working electrode and a counter electrode placed in the aqueous solution, it becomes possible for the probe molecule to stretch/contract.

When the electrodes are provided on a substrate, an adhesive layer may be provided therebetween to enhance adhesion of the electrodes with the substrate. The material, shape, structure, thickness, size and other characteristics of the adhesive layer are not subject to any particular limitation, and may be suitably selected according to the intended purpose. Illustrative examples of suitable materials include chromium and titanium. The structure is not subject to any particular limitation, and may be suitably selected according to the intended purpose. A single layer structure is acceptable, as is also a laminated structure.

The counter electrode is an electrode which is placed opposite the working electrode for the purpose of directly applying a potential therebetween. The shape and material of the counter electrode are not subject to any particular limitation, and may be suitably selected from among known shapes and known materials. Illustrative examples include platinum wire, platinum plate, platinum coil, and gold wire. Nor is there any limitation on the number of counter electrodes, the use of a plurality of counter electrodes being acceptable.

Instead of a two-electrode system, a three-electrode system which uses a reference electrode may be employed in the target molecular evaluation device. The reference electrode is an electrode for regulating the potential between the working electrode and the electrolyte potential. The shape and material of the reference electrode are not subject to any particular limitation, and may be suitably selected from among known shapes and known materials. Illustrative examples include silver-silver chloride (Ag/AgCl) and mercury-mercury chloride ($Hg/Hg_2Cl_2$: saturated calomel electrode). Nor is there any limitation on the number of reference electrodes, the use of a plurality of reference electrode being acceptable.

Voltage Application Means, Signal Detection Means

The voltage application means and the signal detection means are not subject to any particular limitation, and may be suitably selected from among known means.

The AC voltage applied by the voltage applying means is preferably one which includes stepwise or continuous change. The voltage waveform is not subject to any particular limitation, although sine waves or square waves are generally employed. With regard to the voltage value, it is preferable to use a potential range that has been adjusted so as not to break the bond between the probe molecule and the substrate; in the case of a bond between sulfur and the working electrode, the absolute voltage is preferably set to not more than 0.5 V. Here, the "AC voltage" may include a direct-current component. Therefore, cases in which the average voltage is 0 V, cases in which the average is a positive value, and cases in which the average is a negative value are all possible. Although the AC voltage frequency is not subject to any particular limitation, a frequency range that allows formation of an electrical double layer as a source for the electric field (1 MHz or less) is desirable.

When the signal to be detected is fluorescence, a light irradiating means for emitting and quenching fluorescence is required as an auxiliary means. Visible light or ultraviolet light corresponding to the fluorescent marker may be used as this light irradiating means.

When the signal to be detected is a redox current, it is desirable to apply AC voltage that alternates around the redox potential of the redox marker, and observe the redox current.

Marker

The number of markers on a probe molecule is not subject to any particular limitation and may be suitably selected according to the intended purpose. The number is at least one, and may be two or more. The position of the marker on the probe molecule is not subject to any particular limitation, and may be suitably selected according to the intended purpose. In cases where the probe molecule is linear, possible marker positions include the ends thereof. If the probe molecule is a polynucleotide or includes a polynucleotide, the marker position may be at the 3' end or at the 5' end.

Depending on the case, the marker may be added by covalent bonding as part of the target molecule, or may be added by covalent bonding as part of the probe molecule prior to binding with the target molecule. Alternatively, the marker may be included within a nucleotide or the like, as in cases where it is intercalated between adjacent complementary bonds, or it may be integrated as part of a nucleotide or the like by substitution. The marker is preferably positioned so as to be located near an end of the probe molecule.

The marker may be any suitable entity capable of emitting a signal when AC voltage has been applied between the working electrode and the counter electrode, provided it accords with the gist of the embodiments as disclosed in this specification. The signals in this case may include any physical signals, chemical signals or biological signals. Of these, electromagnetic waves and a redox current are preferred. A fluorescent marker that emits fluorescence when excited by the action of electromagnetic waves, particularly light, is especially preferred.

Preferred examples of fluorescent markers include fluorescent dyes, metals and semiconductor nano-particles.

Figure 6:
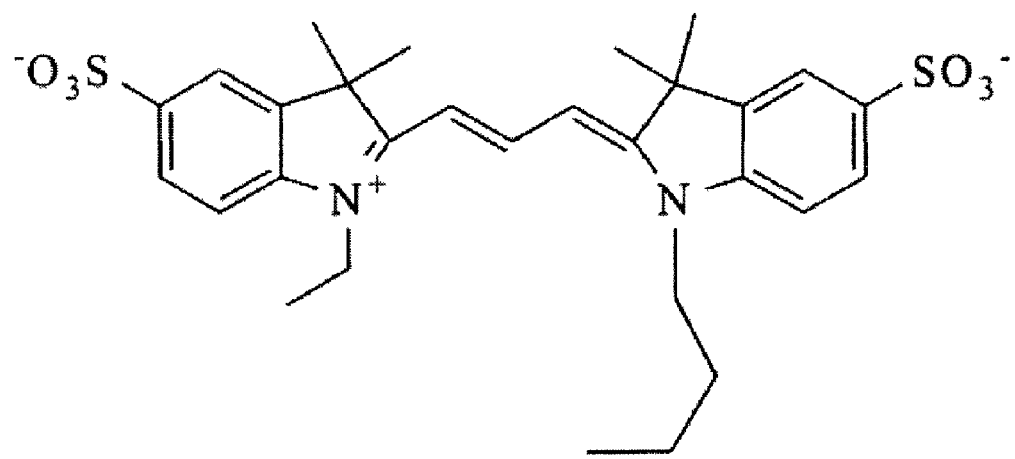
FIG. 6 shows the structural formula of Cy3 as an example of a fluorescent dye.

If the working electrode is a metal, a fluorescent dye which does not emit fluorescence even when irradiated with light of an absorbable wavelength as long as it interacts with the metal (e.g., when positioned near the metal), but which is capable of emitting fluorescence in response to light energy when exposed to light at an absorbable wavelength if it does not interact with the metal (e.g., when positioned away from the metal) is particularly suitable for use as the emitting/quenching member. The fluorescent dye is not subject to any particular limitation, and may be suitably selected from among known fluorescent dyes according to the intended purpose. A preferred example is the compound shown in FIG. 6.

An example of such a marker that may be suitably used is indocarbocyanine 3 (Cy3®).

Figure 7:
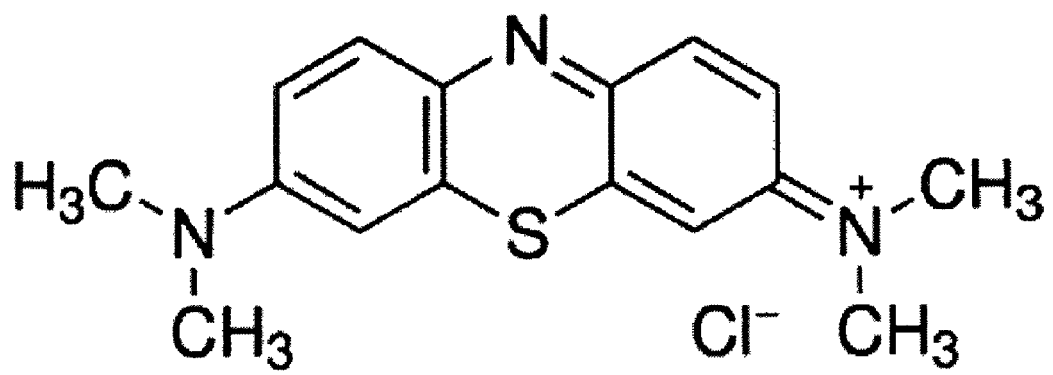
FIG. 7 shows the structural formula of Methylene Blue as an example of a redox marker.
Figure 8:
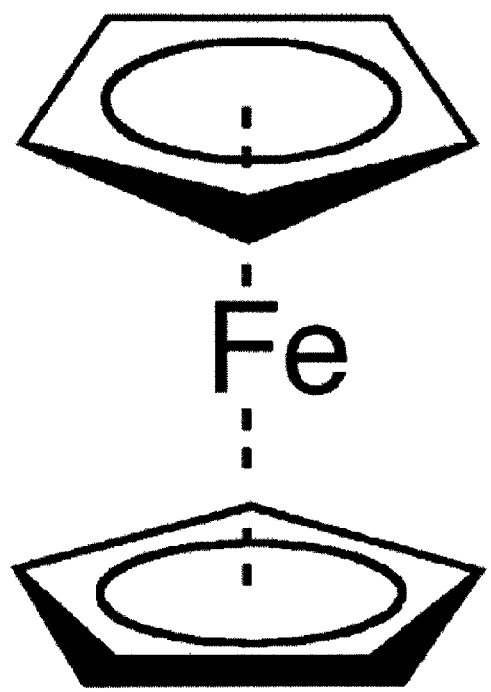
FIG. 8 shows the structural formula of ferrocene as another example of a redox marker.

When the marker is a redox marker, the signal is a redox current. Examples of redox markers include Methylene Blue ($C_{16}H_{18}ClN_3S$; see FIG. 7) and ferrocene ($C_{10}H_{10}Fe$; see FIG. 8).

Changing Frequency of AC Voltage

Figure 3:
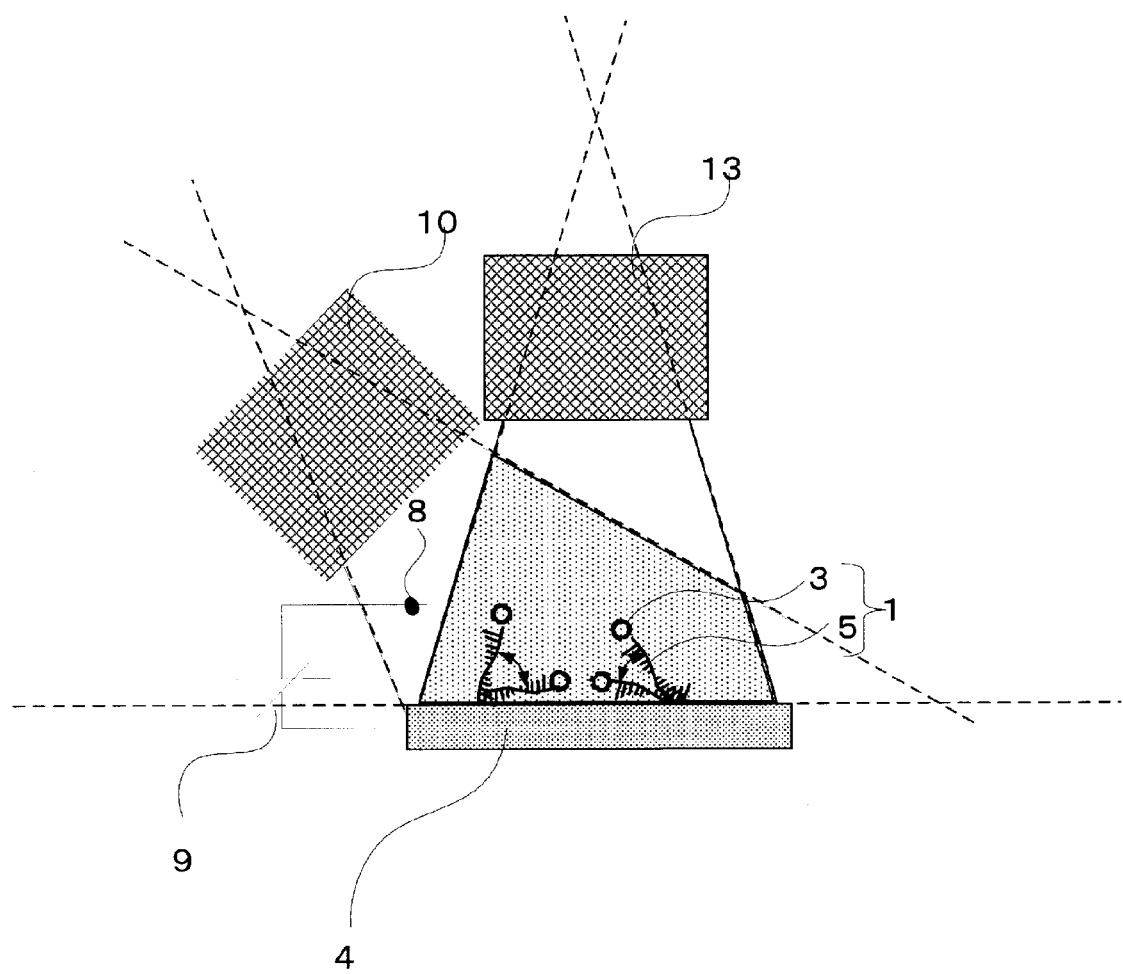
FIG. 3 is a schematic view of the target molecule evaluating device used in Example 1.

The behavior of the resulting fluorescence signals was observed using the target molecule evaluating device shown in FIG. 3. Referring to FIG. 3, a probe molecule 1 with a marker 3 is bound to the working electrode on the substrate 4; the diagram shows how fluorescence that has been excited by a light irradiating means 10 is detected by a fluorescence detecting means 13.

Figure 10:
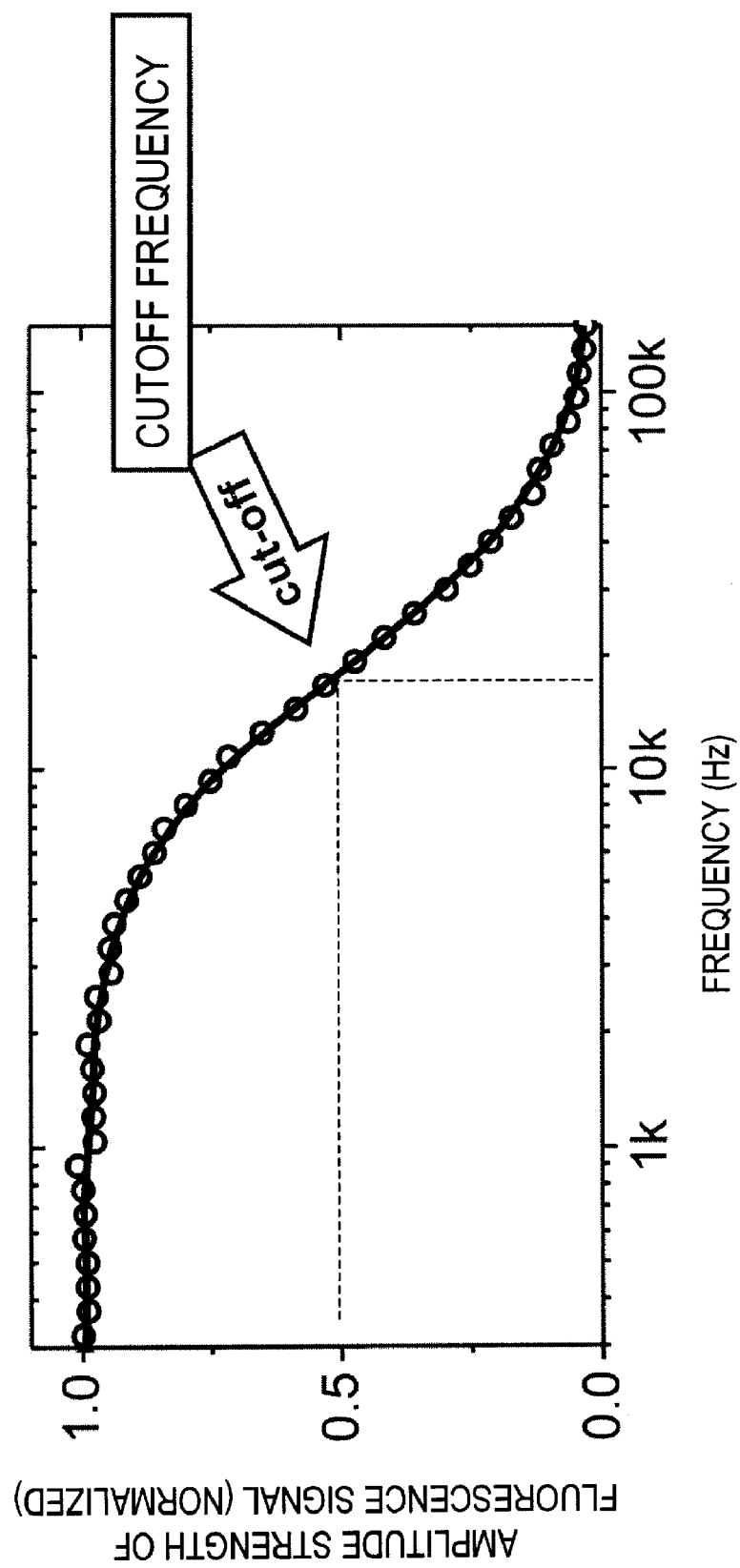
FIG. 10 is a graph showing the amplitude strength versus frequency response of signals from fluorescent labels.

The frequency of the voltage applied was changed under these conditions, and the frequency response of the signals from the fluorescence was recorded, as shown in FIG. 10. FIG. 10 is a graph showing, for ssDNA (single-stranded DNA), the change in the amplitude strength of fluorescence signals when the frequency was changed while applying sine-wave AC voltage. The ssDNA in this case is manipulated at a high speed by increasing the driving frequency. When the frequency is increased even more, the ssDNA becomes unable to follow the driving frequency and the signal amplitude strength decreases, eventually falling to substantially zero (background level). It has already been demonstrated that because the frequency response of this ssDNA is specific to the molecule, when intermolecular interactions which alter these molecular characteristics arise, such as hybridization with complementary stranded DNA or binding with another molecule, such interactions can be detected as a change in the frequency response and used in the evaluation of biomolecules (see claims of Japanese Patent Application No. 2004-238696; claims of Published U.S. Patent Application No. 2005/069932; claims of Japanese Patent Application Laid-open No. 2005-283560; U. Rant et al.: "Dynamic electrical switching of DNA layers on a metal surface," *Nano Lett.* 4, No. 12, 2441-2445 (2004)).

Figure 12:
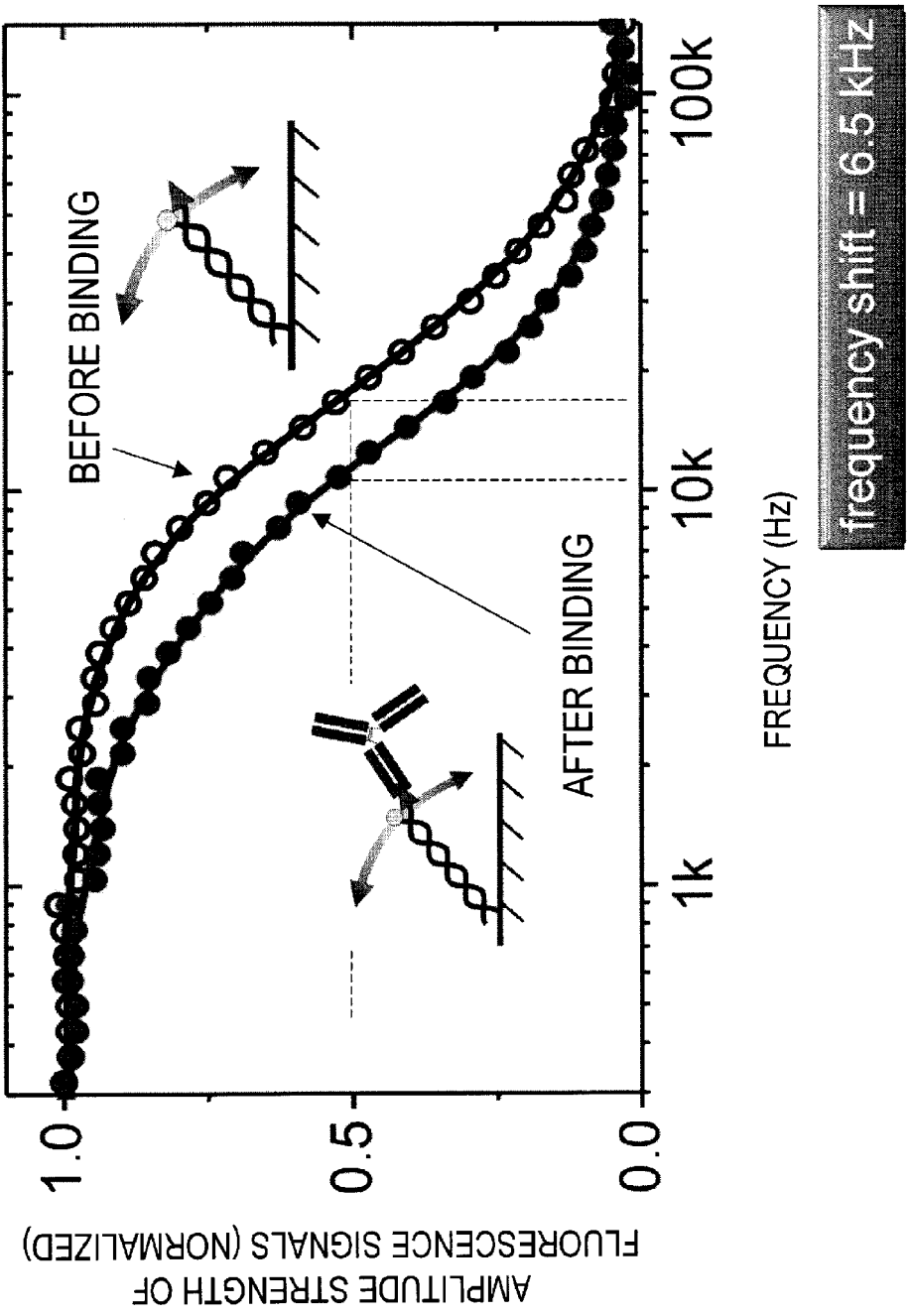
FIG. 12 is a graph showing the behavior of the amplitude strength of marker signals in response to changes in the frequency of the AC voltage in Example 1.

FIG. 12 is a graph showing the change in amplitude strength of fluorescence signals in response to the application of sine-wave AC voltage to dsDNA (double-stranded DNA) having attached at the end a probe molecule which binds with a specific target, and to the same dsDNA when the target has bound to the probe molecule, when the frequency is changed. When the signals before and after target binding are compared with respect to the point at which the signal is one-half the amplitude strength (the cutoff frequency), a shift in cutoff frequency due to target binding is observed.

Figure 4:
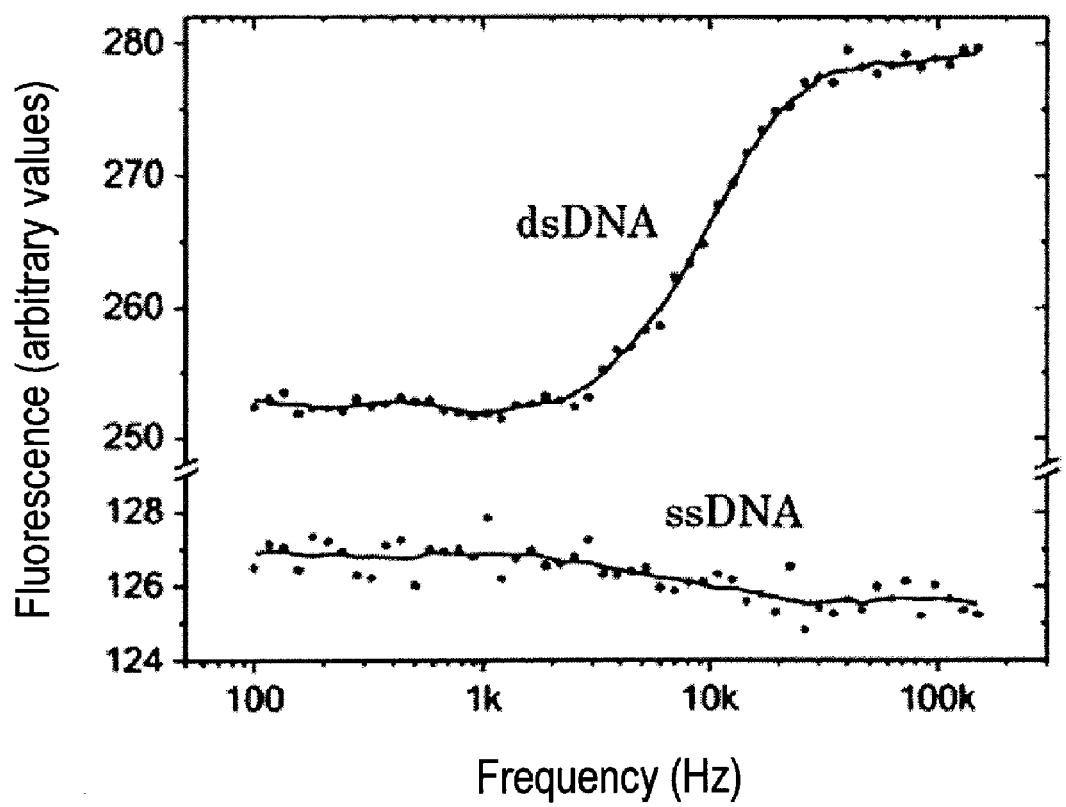
FIG. 4 is a graph showing the behavior of the average value of marker signals in response to changes in the frequency of the AC voltage.

FIG. 4 is a graph plotting the average values of fluorescence intensity for ssDNA (single-strand DNA) and dsDNA (double-strand DNA) when the frequency was changed while applying sine-wave AC voltage. In this case, the ssDNA corresponds to the probe molecule, and the complementary DNA in the dsDNA corresponds to the target molecule. The fluorescence intensity here was the value obtained by averaging the fluorescence intensity of emission and quenching when AC voltage was applied.

It is clear from FIG. 4 that fluorescence intensity declines slightly within the investigated range in the case of ssDNA but rises dramatically past a certain value in the case of dsDNA. This is because the fall time for ssDNA is short compared with the rise time and, conversely, the rise time for dsDNA is shorter than the fall time. Therefore, as the frequency is increased, falls come to dominate in the case of ssDNA, and the average fluorescence intensity decreases. Conversely, rises come to dominate in the case of dsDNA, and the average fluorescence intensity increases (see U. Rant et al.: "Dissimilar kinetic behavior of electrically manipulated single- and double-stranded DNA tethered to a gold surface," *Biophysical Journal* 90, pp. 3666-3671 (2006)).

From these results, it appears that the signal behavior in response to changes in the frequency of the applied voltage should vary also according to the type of probe molecule and the type of target molecule. Such properties may be collectively referred to as the "frequency response."

Therefore, it should be possible to use this frequency response to evaluate the target molecule by separately collecting various types of data and observing the resulting signals. Such evaluation may include molecular weight disparities, shape disparities (e.g., disparities between bulky molecules and molecules which are not bulky, and disparities between linear molecules and branched molecules), disparities in flexibility (the presence of nicks and snips in dsDNA), and charge disparities. Because changes in the behavior of the signal in response to frequency fluctuations are also affected by the amount of probe molecule and target molecule attached per unit surface area, it should also be possible to quantitatively determine the amount of probe molecules and target molecules attached per unit area; that is, to determine the concentration of probe molecules and target molecules.

In addition, determinations of physical values such as the sizes of the molecules and the binding rate, binding rate constant, dissociation rate and dissociation rate constant between the probe molecule and the target molecule may also be carried out. Because the molecule sizes in this case can be regarded as values affected by the steric shapes of the molecules, the electrical charge and other factors, the size of a molecule may be thought of in terms of an effective size, such as the Stokes radius, for example. It has been found from investigations that the Stokes radius is preferred as the effective size.

In a method for evaluating a target molecule bound to a probe molecule having the above marker, such an effective size (e.g., the Stokes radius) can be determined by applying an AC voltage between the working electrode provided on a substrate and the counter electrode, and using the signals, or average values of the signals, obtained from the markers on the probe molecules bound to the working electrode when the frequency of AC voltage is varied.

Any suitable method may be used for determining the effective size using signals or an average value of the signals. Specifically, the effective size may be determined by using one or more target molecule for which the effective size is known. After binding these target molecules to probe molecules having markers, or without binding the target molecules, the signals, or an average value of the signals, obtained from the markers in response to changes in the frequency of AC voltage are determined and, based on these data, the relationship between the change in signals and the effective size at given frequencies are determined. When an unknown target molecule X has been used, the signals obtained from the marker, or an average value of the signals, for the target molecule X bound to the probe molecule having a marker are compared with the signals obtained from the marker, or an average value of the signals, for a probe molecule having a marker not bound to the target molecule. Alternatively, the signals obtained from the marker, or an average value of the signals, for the target molecule X bound to the probe molecule having a marker are compared with the signals obtained from the marker, or an average value of the signals, for another type of known target molecule bound to the probe molecule having a marker. It is possible in this way to determined the effective size.

In cases where one wishes to determine the effective size to a high accuracy, it would commonly be thought preferable to use the same marker and the same probe molecule, and for the target molecule X to have a shape which resembles the shape of a known target molecule. However, as shown in the subsequently described examples, given that a good linear relationship is obtained even when with the use of differing probe molecules or of a target molecule of differing shape, these factors appears to have only a small influence. Moreover, regarding the types of markers and probe molecules, when means of correction based on differences therebetween are conceivable, it is possible to reduce the influence of such differences. In the case of markers, given that changing the type of marker alters the intensity of the fluorescence emitted, there will indeed be times where the particular marker used will have a large influence. However, because such influences are small when it comes to the type of probe molecule, there seems to be a large degree of freedom for changing the type of probe molecule.

More concrete methods for determining the effective size are described in detail in the subsequent examples.

In the above-described method for evaluating a target molecule bound to a probe molecule having a marker, determinations of the binding rate, binding rate constant, dissociation rate and dissociation rate constant between a probe molecule and a target molecule can be carried out using the signals, or an average value of the signals, obtained from markers on probe molecules bound to the working electrode in response to changes in frequency when AC voltage is applied between the working electrode provided on a substrate and a counter electrode.

Specifically, by continuously supplying target molecules to probe molecules having markers, causing the target molecules to bind to the probe molecules, and observing the changes over time in signals obtained from the markers, or an average values of the signals, it is possible to determine the binding rate and binding rate constant between the probe molecules and the target molecules. Also, by continuously supplying a suitable medium such as a solvent to a state in which target molecules are bound to probe molecules with markers, causing the target molecules to dissociate from the probe molecules, and observing the changes over time in signals obtained from the markers, or an average value of the signals, it is possible to determine the dissociation rate and dissociation rate constant between the probe molecules and the target molecules. In "continuously supplying" target molecules as mentioned above, allowance can often be made for interruptions to measure the signals obtained from the markers. As such, in the embodiments described in this specification, instances where interruptions occur for such a purpose also fall within the scope of what is meant by "continuously supplying."

No particular limitation is imposed on the method used to change the frequency of the AC voltage applied when making determinations of the foregoing physical properties. Such a method should be suitably selected, then investigated to determine whether useful signal behavior by the markers is indeed observed. When a large change is predicted, such as in the case of dsDNA in FIG. 4, it is possible that a single stepwise change to a different frequency will suffice. It is also useful to investigate, by means of multi-step changes, what kinds of signal changes are observed at what frequencies. In addition, finer signal changes may be achieved by continuously varying the frequency.

EXAMPLES

Examples and comparative examples are given below by way of illustration.

Example 1

Detection of Target Molecule Size Differences Using Frequency Response

FIG. 3 shows the configuration of an apparatus necessary for carrying out the embodiments disclosed in this specification. FIG. 3 is a schematic diagram illustrating an example of an apparatus wherein a probe molecule 1 having on the molecule a fluorescent dye (fluorescent label; i.e., a marker) 3 is fixed (bound) to a gold electrode (working electrode, not shown) on a substrate 4, an optical fiber (incident light fiber) 10 is used to expose the probe molecule to light of a wavelength that excites the fluorescent dye and is capable of eliciting emission/quenching, and an optical fiber (light-receiving fiber) 13 is provided to detect light emission/quenching from the fluorescent dye.

An AC power supply capable of high-frequency driving to the solution potential and a DC power supply for applying an offset potential were connected to the gold electrode.

An example is shown here of a method for evaluating the differences when molecules of differing sizes (effective values) were used as the target.

Figure 11:
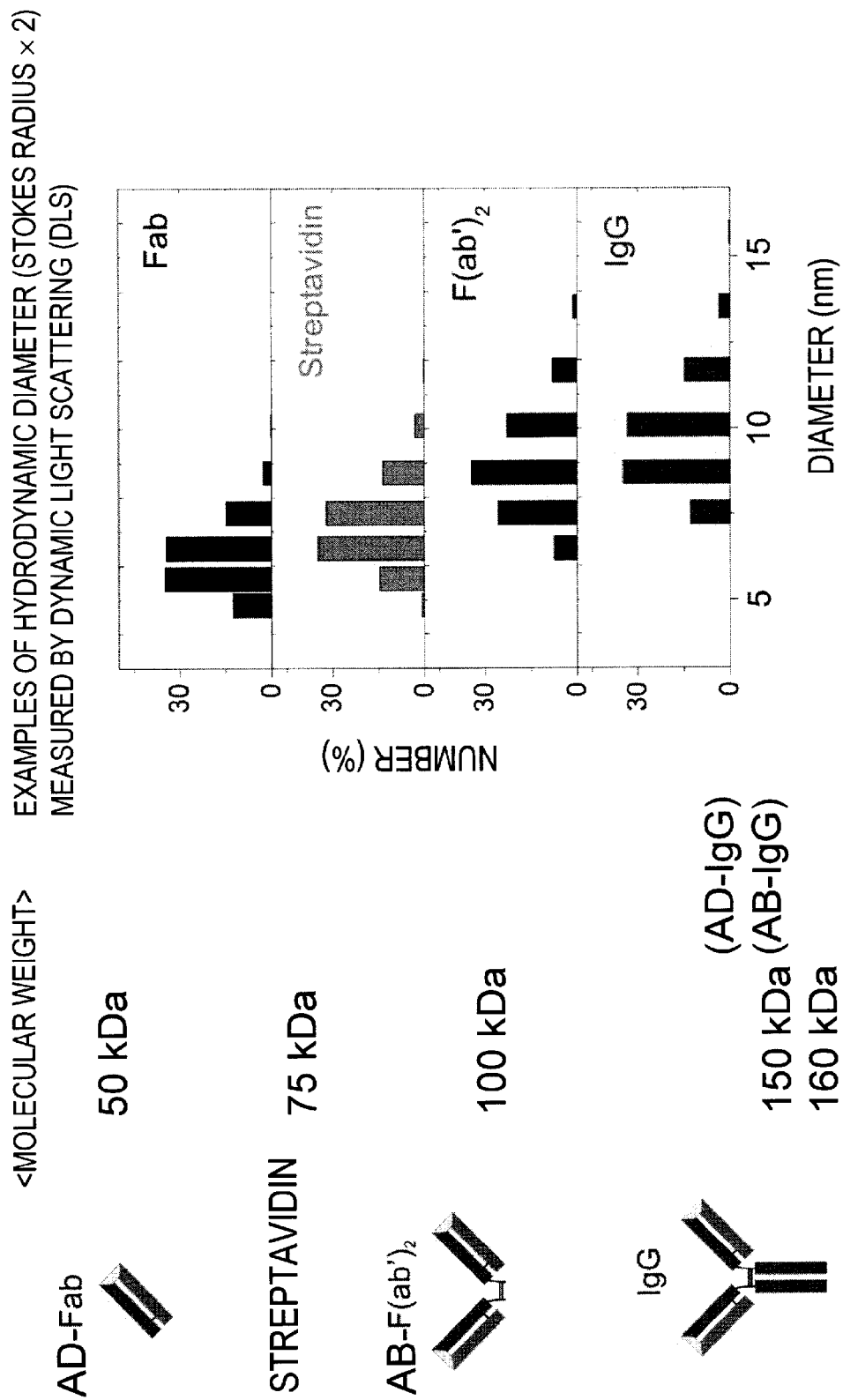
FIG. 11 shows the target molecules of differing molecular weights used in Examples 1 and 4 and their effective sizes (diameters in solution)

In FIG. 11, the types and molecular weights of the molecules are shown on the left side, and the hydrodynamic diameters (effective diameters, including associated ions, in solution) obtained by the DLS method are shown as the size (effective value) of the target molecule on the right side. The weighted average of the hydrodynamic diameter was twice the Stokes radius.

Using single-stranded DNA (72-base probe DNA: ss 72-mer probe DNA) having a thiol group (—SH) at one end and a fluorescent cyanine dye (Cy3) at the other end as the above-mentioned fluorescent pigment, the DNA was fixed (bound) via sulfur atoms by self-assembly onto a gold electrode (0.5 mm diameter) using the method described in A. Ulman (in "Formation and structure of self-assembled monolayers," Chem. Rev. 96, No. 4, pp. 1533-1554 (1996)), thereby forming on the gold electrode a molecular film of the above DNA. In addition, complementary-strand DNA having at one end a probe molecule which binds specifically with a target molecule and the above DNA that had been fixed to the substrate were hybridized, forming double-stranded DNA. The hybridization conditions consisted of holding 1 μM of the complementary-strand DNA in a buffer solution (10 mM Tris, 200 mM NaCl, pH 7.3) for one hour, then rinsing with a buffer solution (10 mM Tris, 50 mM NaCl, pH 7.3) containing no complementary-strand DNA, thereby forming on the substrate double-stranded DNA having fluorescent dye and a probe molecule. Antidigoxigenin Fab fragment (AD-Fab), antibiotin F (ab')$_2$ fragment (AB-F(ab')$_2$), antidigoxigenin IgG (AD-IgG) and antibiotin IgG (AB-IgG) (see right side of FIG. 14) were used as the targets of differing molecular weights, digoxigenin was used as the probe molecule for AD-Fab and AD-IgG, and biotin was used as the probe molecule for AB-F (ab')$_2$ and AB-IgG.

An AC electric field (sine wave, E=−0.15±0.25 V$_{rms}$) was applied between the gold electrode to which the DNA was fixed and a platinum electrode as the counter electrode, during which time the signals from the fluorescent label were observed. The frequency of the AC electric field was varied, and the amplitude strength (normalized value of the difference obtained by subtracting the minimum value from the maximum value at each frequency) of signals from the fluorescent label when driven by the AC electric field from a low frequency of 10 Hz to a high frequency of 150 kHz were recorded. A buffer solution (10 mM Tris, 50 mM NaCl, pH 7.3) was used for measurement. As an example, the results for the digoxigenin probe molecule are plotted in FIG. 12 as the "before binding" curve.

Next, a target molecule (AD-IgG) was bound to the probe molecule of the above double-stranded DNA fixed to the substrate. The binding conditions consisted of holding 50 nM of the target molecule in a buffer solution (10 mM Tris, 200 mM NaCl, pH 7.3) for one hour, then rinsing with a buffer solution (10 mM Tris, 50 mM NaCl, pH 7.3) containing no target molecules. Next, the frequency of the AC electric field was changed in the same way as in the above-described measurement method, during which time the amplitude strength of the signals from the fluorescent label (fluorescent dye) was recorded. The results are plotted as the "after binding" curve in FIG. 12.

Figure 13:
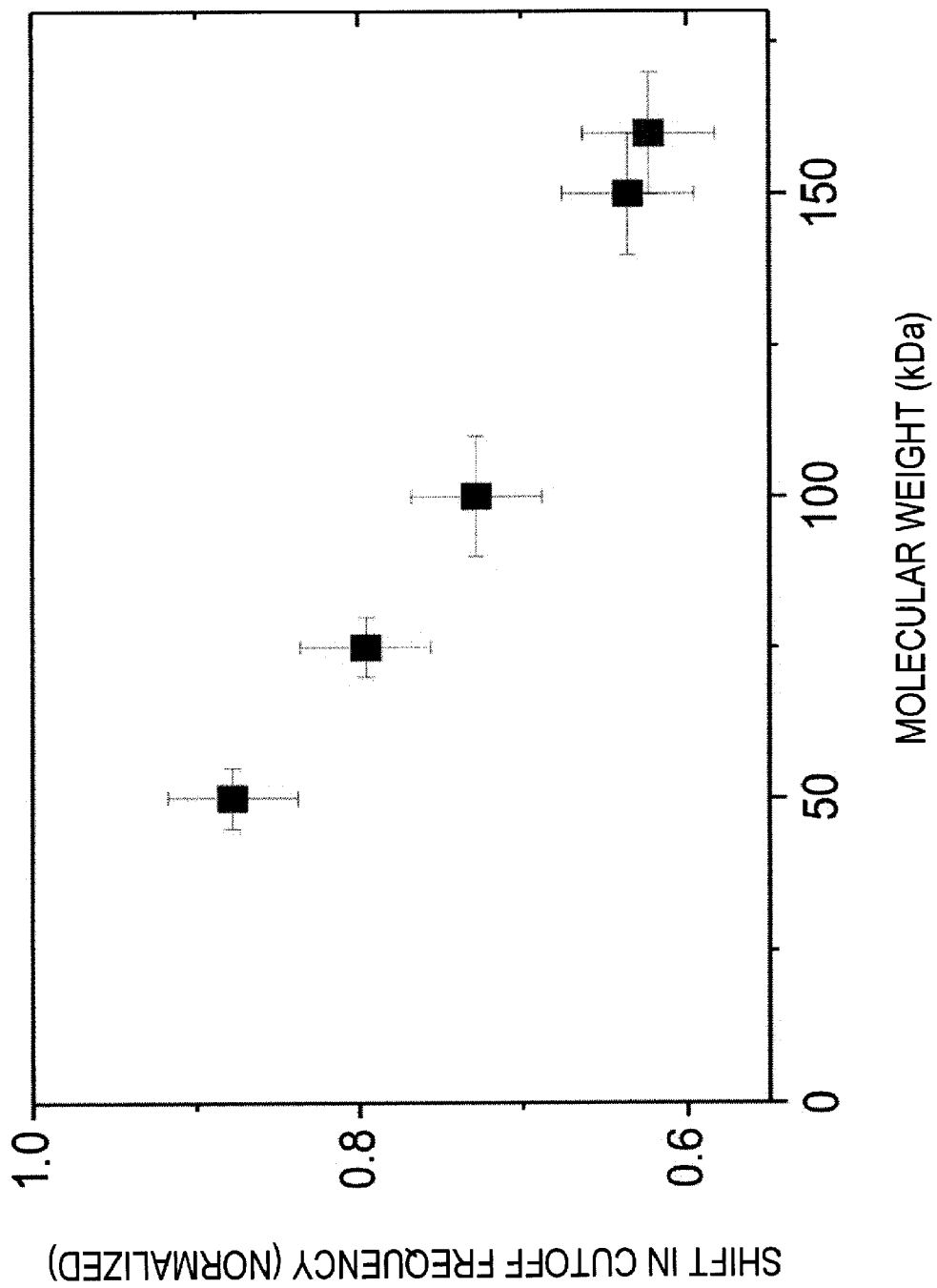
FIG. 13 is a graph showing the relationship between the shift in cutoff frequency of signals (amplitude strength) from the fluorescent labels obtained in FIG. 12 and molecular weight.

As is apparent from FIG. 12, the behaviors before and after binding of the target molecule were completely different on the high-frequency side, and the cutoff frequencies were found to differ. FIG. 13 plots the relationship between the shift in cutoff frequency and the molecular weight of the target molecule when the above experiment was carried out using target molecules of different molecular weights. It is apparent from FIG. 13 that the amount of change differs with the effective size of the molecules.

Therefore, by observing the response of the signals from the fluorescent labels to the driving frequency, it is possible to detect differences in the sizes of target molecules in a target solution. In such a case, there is no need to label the target molecules.

Example 2

Detection of Double-Stranded DNA Using Average Values of Signals

Next, an example is given in which complementary-strand DNA is detected using average values of the fluorescence signal frequency response.

In this example, an apparatus having the same configuration as that shown in FIG. 3 for Example 1 was used.

Using single-stranded DNA (48-base probe DNA: ss 48-mer probe DNA) having a thiol group (—SH) at one end and a fluorescent cyanine dye (Cy3) at the other end as the above-mentioned fluorescent pigment, the DNA was fixed (bound) via sulfur atoms by self-assembly onto a gold electrode (0.5 mm diameter) using the method described in A. Ulman: "Formation and structure of self-assembled monolayers," Chem. Rev. 96, No. 4, pp. 1533-1554 (1996), thereby forming on the gold electrode a molecular film of the above DNA.

An AC electric field (sine wave, E=−0.15±0.25 V$_{rms}$) was applied between the gold electrode to which the DNA was fixed and a platinum electrode as the counter electrode, during which time the signals from the fluorescent label were observed. The frequency of the AC electric field was varied, and the average value of signals from the fluorescent label when driven by the AC electric field from a low frequency of 100 Hz to a high frequency of 150 kHz (actually, signals having a frequency of 1 Hz, which is sufficiently lower than the driving frequency) were recorded. A buffer solution (10 mM Tris, 50 mM NaCl, pH 7.3) was used for measurement. The results are plotted as "ssDNA" in FIG. 4.

Next, the above DNA fixed to the substrate was specifically hybridized with non-labeled complementary-strand DNA to form double-stranded DNA. The hybridization conditions consisted of holding 1 μM of the complementary strand DNA in a buffer solution (10 mM Tris, 200 mM NaCl, pH 7.3) for one hour, then rinsing with a buffer solution (10 mM Tris, 50 mM NaCl, pH 7.3) containing no complementary strand DNA. Next, the frequency of the AC electrical field was changed in the same way as in the above-described measurement method, during which time the signals from the fluorescent label (fluorescent dye) were recorded. The results were plotted as the "dsDNA" curve in FIG. 4. As is apparent from FIG. 4, ssDNA and dsDNA have completely different behaviors on the high-frequency side.

Here, in a case where complementary strand DNA was the target molecule to be evaluated, by observing the response of the signals from the fluorescent label to the driving frequency, it is possible to detect whether the target molecule is present or absent in the test solution. In such a case, there is no need to label the target molecules.

The signals from the fluorescent labels, being distinctive signals which reflect the kinetic properties of the ssDNA or dsDNA molecules, have the advantage of a high selectivity and low noise owing to the fact that, in evaluating the target, it is possible to avoid the influence of co-existing contaminants from adversely affecting evaluation and the mis-detection of nonspecifically adsorbed target.

In this example, 1 Hz signals are recorded as the average value of signals from the fluorescent label, but any frequency that is sufficiently low compared with the driving frequency may be used and may be recorded continuously (DC). Although the response of the DNA to the driving frequency was closely measured from 100 Hz to 150 kHz, as is apparent from FIG. 4, evaluation of the target molecule is also possible by observing the frequencies at any two or more points where there is a significant difference. In cases where signal changes before and after binding of the target molecule are predictable beforehand, or where the changes are already known due to preliminary experiments, there is no need to evaluate the signals before and after binding; the presence or absence of the target molecule can be determined by evaluating only the signals after an experiment which corresponds to binding of the target molecule.

Also, in this example, the probe molecule is ssDNA and the target molecule is the complementary strand DNA thereto, although anything may be used as the target, provided there is a difference between the response to the driving frequency by the probe molecule and the response by the target molecule bound to the probe molecule.

Example 3

Detecting the Presence/Absence of a Target Molecule Using Average Value of Signals FIG. 2 is a diagram showing the required device configuration. FIG. 2 is a schematic diagram illustrating an example of an apparatus wherein a probe molecule 1 having on the molecule a fluorescent dye (fluorescent label; i.e., marker) 3 and a target molecule binding part 6 which binds specifically with a target molecule 7 is fixed (bound) to a gold electrode 2 on a substrate 4, an optical fiber (incident light fiber) 10 is used to expose the probe molecule to light of a wavelength that excites the fluorescent dye and is capable of eliciting emission/quenching, and an optical fiber (light-receiving fiber, not shown) is provided to detect light emission/quenching from the fluorescent dye.

An AC power supply capable of high-frequency driving to the solution potential and a DC power supply for applying an offset potential were connected to the gold electrode.

Figure 9:
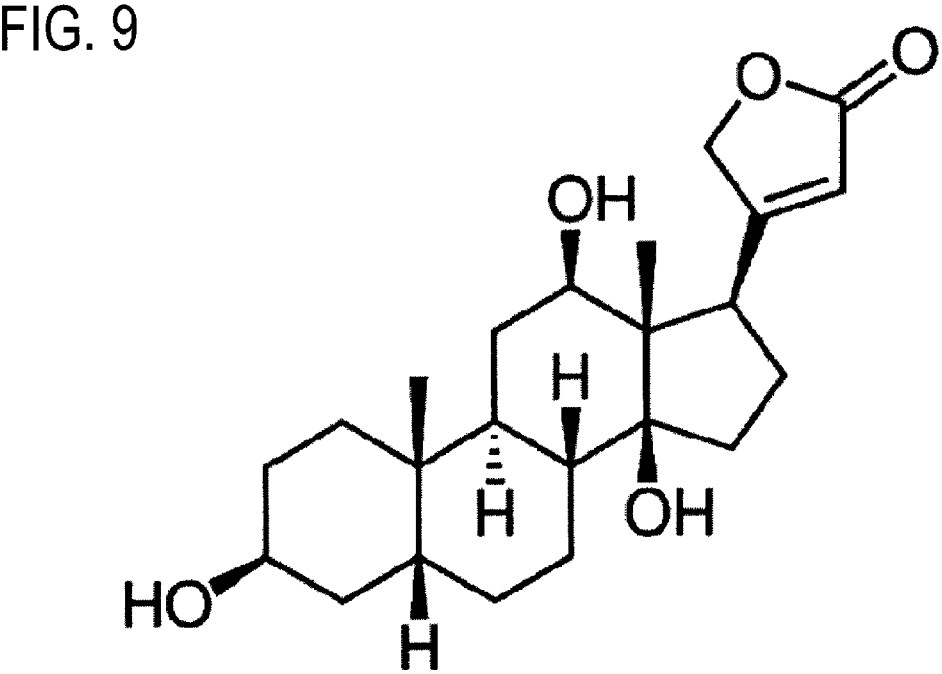
FIG. 9 shows the structural formula of the digoxigenin used in Example 3.

Using single-stranded DNA (48-base probe DNA: ss 48-mer probe DNA) having a thiol group (—SH) at one end and a fluorescent cyanine dye (Cy3) at the other end as the above-mentioned fluorescent pigment, the DNA was fixed (bound) via sulfur atoms by self-assembly onto the gold electrode (0.5 mm diameter) using the method described in A. Ulman (in "Formation and structure of self-assembled monolayers," *Chem. Rev.* 96, No. 4, pp. 1533-1554 (1996)), thereby forming on the gold electrode a molecular film of the above DNA. In addition, complementary-strand DNA having at one end a probe molecule (digoxigenin; see FIG. 9) which binds specifically with a target molecule (antidigoxigenin) and the above DNA that had been fixed to the substrate were hybridized, forming double-stranded DNA. The hybridization conditions consisted of holding 1 μM of the complementary-strand DNA in a buffer solution (10 mM Tris, 200 mM NaCl, pH 7.3) for one hour, then rinsing with a buffer solution (10 mM Tris, 50 mM NaCl, pH 7.3) containing no complementary-strand DNA, thereby forming on the substrate double-stranded DNA having fluorescent dye and a probe molecule.

Figure 5:
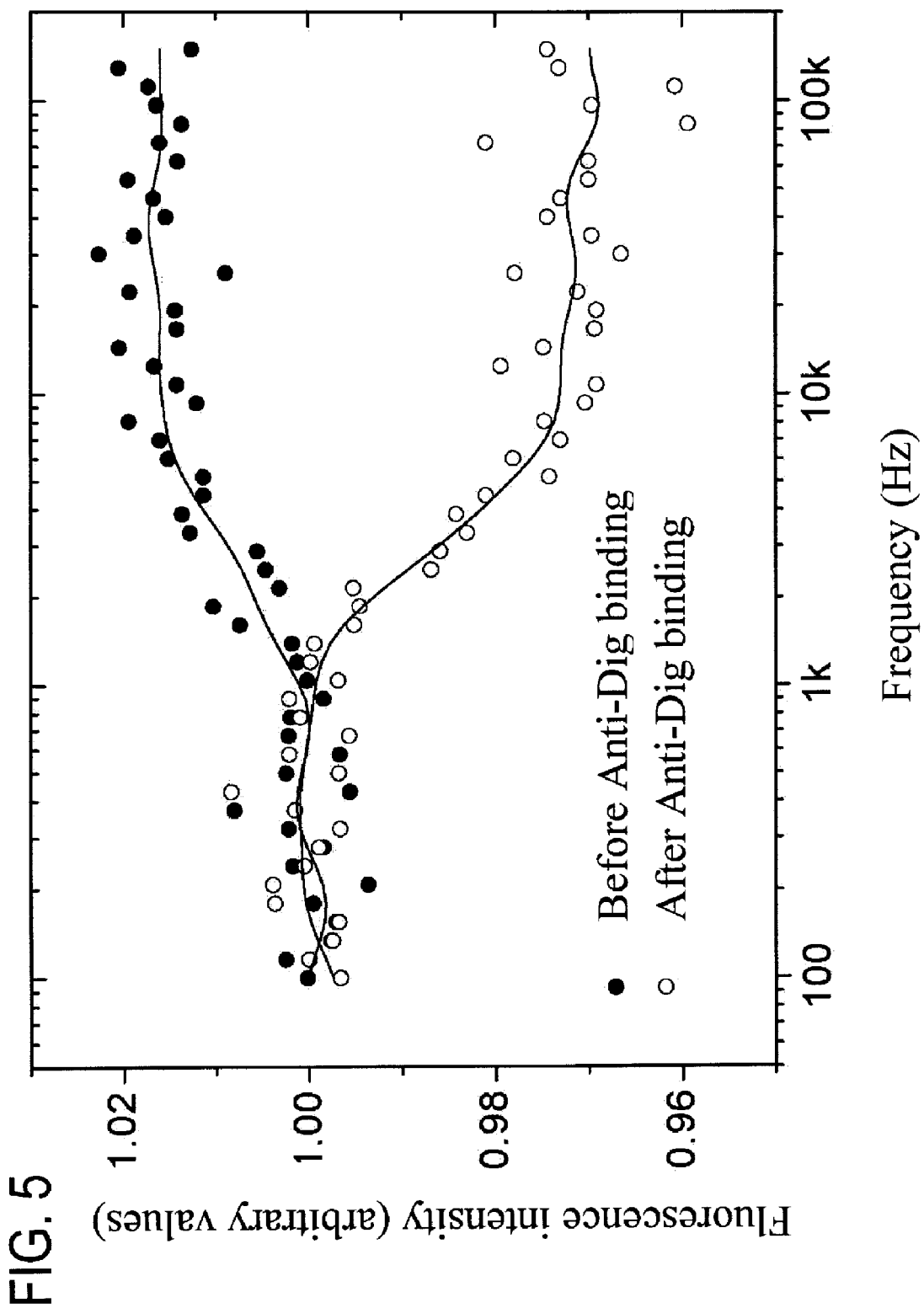
FIG. 5 is a graph showing the behavior of the average value of marker signals in response to changes in the frequency of the AC voltage in Example 3.

An AC electric field (sine wave, E=−0.15±0.25 V$_{rms}$) was applied between the gold electrode to which the DNA was fixed and a platinum electrode as the counter electrode, during which time the signals from the fluorescent label were observed. The frequency of the AC electric field was varied, and the average value of the fluorescent label signals when driven by the AC electric field from a low frequency of 100 Hz to a high frequency of 150 kHz (actually, signals having a frequency of 1 Hz, which is sufficiently lower than the driving frequency) were recorded. A buffer solution (10 mM Tris, 50 mM NaCl, pH 7.3) was used for measurement. The results are plotted as "Before AntiDig binding" in FIG. 5.

Next, a target molecule was bound to the probe molecule of the above double-stranded DNA fixed to the substrate. The binding conditions consisted of holding 50 nM of the target molecule in a buffer solution (10 mM Tris, 200 mM NaCl, pH 7.3) for one hour, then rinsing with a buffer solution (10 mM Tris, 50 mM NaCl, pH 7.3) containing no target molecules. Next, the frequency of the AC electric field was changed in the same way as in the above-described measurement method, during which time the signals from the fluorescent label (fluorescent dye) were recorded. The results were plotted as the "After AntiDig binding" curve in FIG. 5. As is apparent from FIG. 5, the before target binding signals and the after target binding signals have completely different behaviors on the high-frequency side.

Here, by observing the response of the signals from the fluorescent label to the driving frequency, it is possible to detect whether the target molecules are present or absent in the test solution. In such a case, there is no need to label the target molecules.

The signals from the fluorescent labels, being distinctive signals which reflect the kinetic properties of molecules before and after target binding, have the advantage of a high selectivity and low noise owing to the fact that, in evaluating the target, it is possible to avoid both the influence of co-existing contaminants from adversely affecting evaluation and the mis-detection of nonspecifically adsorbed target.

In this example, 1 Hz signals are recorded as the average value of signals from the fluorescent label, but any frequency that is sufficiently low compared with the driving frequency may be used and may be recorded continuously (DC). Although the response of the DNA to the driving frequency was closely measured from 100 Hz to 150 kHz, as is apparent from FIG. 5, evaluation of the target molecule is also possible by observing the frequencies at any two or more points where there is a significant difference. In cases where signal changes before and after binding of the target molecule are predictable beforehand, or in cases where the changes are already known due to preliminary experiments, there is no need to evaluate the signals before and after binding; the presence or absence of the target molecule can be ascertained by evaluating only the signals after an experiment that corresponds to binding of the target molecule.

Also, in this example, the probe molecule is DNA with digoxigenin attached and the target molecule is antidigoxigenin, although anything may be used as the target, provided there is a difference between the response to the driving frequency by the probe molecule and the response by the target molecule bound to the probe molecule.

Example 4

Detecting Size Differences in Target Molecules Using Average Values of Signals

This example has to do with a method in which molecules of differing sizes (effective values) serve as the targets, and those differences are evaluated using average values of the fluorescent signals. In FIG. 11, the types and molecular weights of the molecules are shown on the left side, and the hydrodynamic diameters (effective diameter, including associated ions, in solution) obtained by the DLS method are shown as the size (effective value) of the target molecule on the right side. The weighted average of the hydrodynamic diameter was twice the Stokes radius.

In this example, an apparatus having the same configuration as that shown in FIG. 2 for Example 3 was used. Unless noted otherwise, the conditions of use were the same as in Example 3.

Using single-stranded DNA (72-base probe DNA: ss 72-mer probe DNA) having a thiol group (—SH) at one end and a fluorescent cyanine dye (Cy3) at the other end as the above-mentioned fluorescent pigment, the DNA was fixed (bound) via sulfur atoms by self-assembly onto a gold electrode (2 mm diameter) using the method described in A. Ulman in ("Formation and structure of self-assembled monolayers," Chem. Rev. 96, No. 4, pp. 1533-1554 (1996)), thereby forming on the gold electrode a molecular film of the above DNA. In addition, complementary-strand DNA having at one end a probe molecule which binds specifically with a target molecule and the above DNA that had been fixed to the substrate were hybridized, forming double-stranded DNA. The hybridization conditions consisted of holding 1 μM of the complementary-strand DNA in a buffer solution (10 mM Tris, 200 mM NaCl, pH 7.3) for one hour, then rinsing with a buffer solution (10 mM Tris, 50 mM NaCl, pH 7.3) containing no complementary-strand DNA, thereby forming on the substrate double-stranded DNA having fluorescent dye and a probe molecule. Antidigoxigenin Fab fragment (AD-Fab), antibiotin F (ab')$_2$ fragment (AB-F(ab')$_2$) and antibiotin IgG (AB-IgG) (see right side of FIG. 14) were used as the targets of differing molecular weights, digoxigenin was used as the probe molecule for AD-Fab, and biotin was used as the probe molecule for AB-F(ab')$_2$ and AB-IgG.

An AC electric field (sine wave, E=−0.15±0.25 $V_{rms}$) was applied between the gold electrode to which the DNA was fixed and a platinum electrode as the counter electrode, during which time the signals from the fluorescent label were observed. The frequency of the AC electric field was varied, and the average value of the fluorescent label signals when driven by the AC electric field from a low frequency of 100 Hz to a high frequency of 150 kHz (actually, signals having a frequency of 1 Hz, which is sufficiently lower than the driving frequency) was recorded. A buffer solution (10 mM Tris, 50 mM NaCl, pH 7.3) was used for measurement. The results were plotted as "before target molecule binding" curves (DNA-tag) in FIG. 14. The shapes of these target molecules are shown schematically on the right side of FIG. 14.

Next, target molecules were bound to the probe molecules of the above double-stranded DNA fixed to the substrate. The binding conditions consisted of holding 50 nM of the target molecule in a buffer solution (10 mM Tris, 200 mM NaCl, pH 7.3) for one hour, then rinsing with a buffer solution (10 mM Tris, 50 mM NaCl, pH 7.3) containing no target molecules. Next, the frequency of the AC electrical field was changed in the same way as in the above-described measurement method, during which time the signals (average value) from the fluorescent label (fluorescent dye) were recorded. The results were plotted as "after binding" curves (DNA-D & AD-Fab, DNA-B & AB-F(ab')$_2$, and DNA-B & AB-IgG) in FIG. 14. Here, "DNA-D" refers to DNA-tag in which the probe molecule is digoxigenin (D), and "DNA-B" refers to DNA-tag in which the probe molecule is biotin (B).

Figure 14:
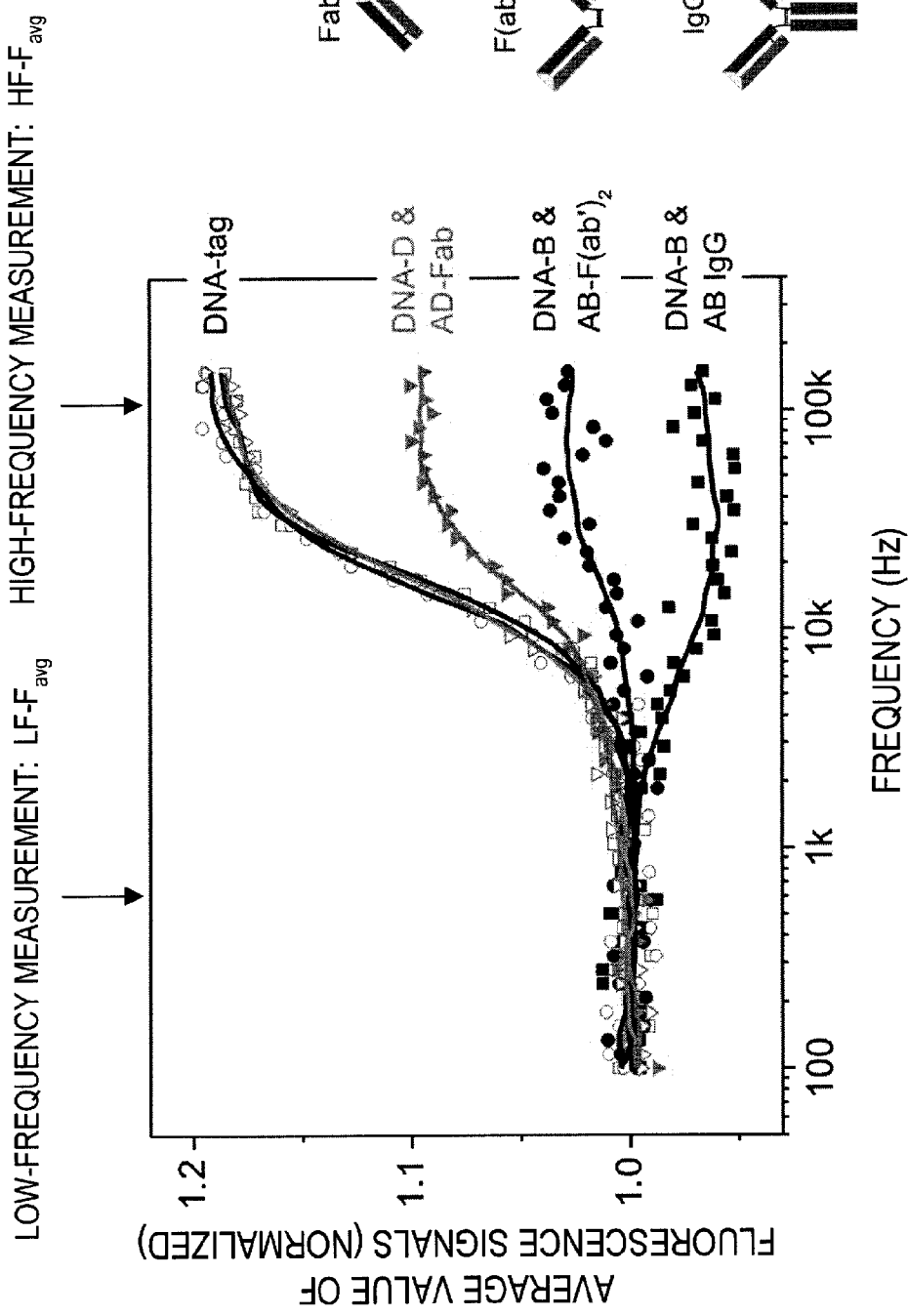
FIG. 14 is a graph showing the marker signal behavior in response to changes in the AC voltage frequency in Example 4.

As is apparent from FIG. 14, the behaviors before and after binding of the target molecule were completely different. Moreover, it can be seen that the amount of change differs with the effective size of the molecules.

Therefore, by observing the response of the signals from the fluorescent labels to the driving frequency, it is possible to detect differences in the sizes of the target molecules in a target solution. In such a case, there is no need to label the target molecules.

Figure 15:
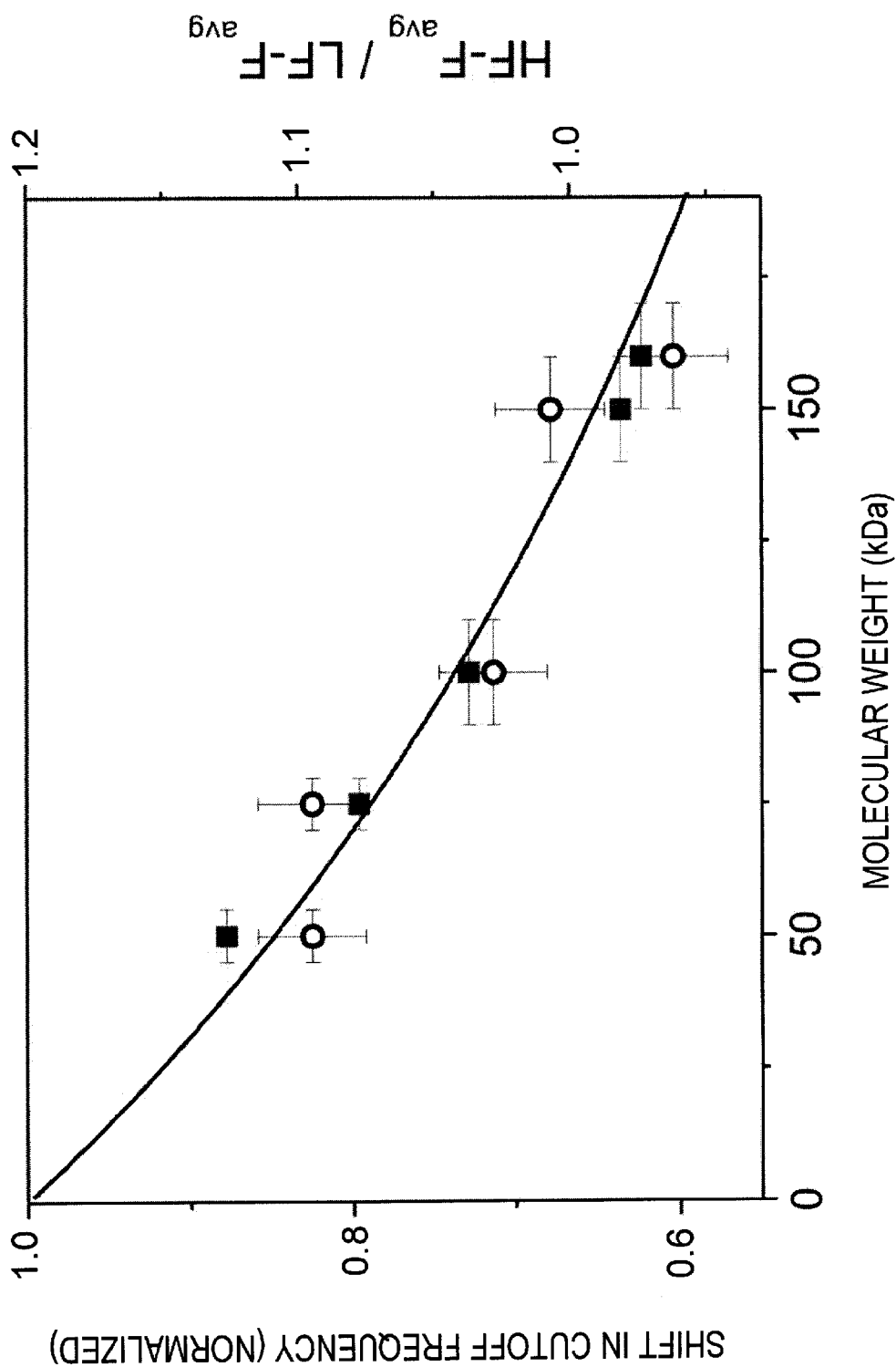
FIG. 15 is a graph showing the relationship between the high-frequency response to low-frequency response ratio for the signals (average values) from fluorescent labels obtained in FIG. 14 and the molecular weight. The plot from FIG. 13 is also shown for comparison.

To give a specific example, FIG. 15 shows the relationship between the ratio (HF-$F_{avg}$/LF-$F_{avg}$) of the average value HF-$F_{avg}$ of signals from fluorescent labels at the high frequency (100 kHz) in FIG. 14 to the average value LF-$F_{avg}$ of signals from fluorescent labels at the low frequency (800 Hz) and molecular weight. The shift in the cutoff frequency of the amplitude strength, i.e., the frequency response observed in Example 1, is also shown here for the purpose of comparison. This graph shows that, even though the probe molecules are different, and even though the types and shapes of the target molecules vary considerably, there exists a clear relationship between the amount of change in the signals and the molecular weight.

Thus, for instance, for the same marker and the same probe molecule, when signals (average value) are obtained from similar fluorescent labels using a target molecule (target molecule X) which differs from the target molecule of the present example, the molecular weight of the target molecule X can be determined using the relationship shown in FIG. 15.

The signals from the fluorescent label, being distinctive signals which reflect the kinetic properties of the molecules before and after binding of the target molecule, have the advantage of a high selectivity and low noise owing to the fact that, in evaluating the target, it is possible to avoid the influence of co-existing contaminants from adversely affecting evaluation and the mis-detection of nonspecifically adsorbed target.

In this example, 1 Hz signals are recorded as the average value of signals from the fluorescent label, but any frequency that is sufficiently low compared with the driving frequency may be used. Although the response of the DNA to the driving frequency was closely measured from 100 Hz to 150 kHz, as is apparent from FIG. 14, evaluation of the target molecule is also possible by observing the frequencies at any two or more points where there is a significant difference. In cases where signal changes before and after binding of the target molecule are predictable beforehand, or where the changes are already known due to preliminary experiments, there is no need to evaluate the signals before and after binding; the molecular weight (effective size) of the target molecule can be evaluated by evaluating only the signals after an experiment which corresponds to binding of the target molecule.

Moreover, in the present example, the probe molecule is digoxigenin or biotin and the target molecule is the antidigoxigenin Fab fragment, the antibiotin F(ab')$_2$ fragment or antibiotin, although anything may be used as the target, provided there is a difference between the response to the driving frequency by the probe molecule and the response by the target molecule bound to the probe molecule.

Example 5

Detecting Changes Over Time in Target Molecule Using Average Value of Signals

In this example, an apparatus having the same configuration as that shown in FIG. 2 for Example 4 was used. Unless noted otherwise, the conditions of use were the same as in Example 4.

Using single-stranded DNA (72-base probe DNA: ss 72-mer probe DNA) having a thiol group (—SH) at one end and a fluorescent cyanine dye (Cy3) at the other end as the above-mentioned fluorescent pigment, the DNA was fixed (bound) via sulfur atoms by self-assembly onto a gold electrode (0.5 mm diameter) using the method described in A. Ulman in ("Formation and structure of self-assembled monolayers," *Chem. Rev.* 96, No. 4, pp. 1533-1554 (1996)), thereby forming on the gold electrode a molecular film of the above DNA. In addition, complementary-strand DNA having at one end a probe molecule which binds specifically with a target molecule and the above DNA that had been fixed to the substrate were hybridized, forming double-stranded DNA. The hybridization conditions consisted of holding 1 µM of the complementary-strand DNA in a buffer solution (10 mM Tris, 200 mM NaCl, pH 7.3) for one hour, then rinsing with a buffer solution (10 mM Tris, 50 mM NaCl, pH 7.3) containing no complementary-strand DNA, thereby forming on the substrate double-stranded DNA having fluorescent dye and a probe molecule. Antibiotin IgG (AB-IgG) was used as the target molecule, and biotin was used as the probe molecule of AB-IgG.

An AC electric field (sine wave, $E=-0.15\pm0.25\ V_{rms}$) was applied between the gold electrode to which the DNA was fixed and a platinum electrode as the counter electrode, during which time the signals from the fluorescent label were observed. The frequency of the AC electric field was varied, and the average value of the fluorescent label signals when driven by the AC electric field from a low frequency of 100 Hz to a high frequency of 150 kHz (actually, signals having a frequency of 1 Hz, which is sufficiently lower than the driving frequency) was recorded. A buffer solution (10 mM Tris, 50 mM NaCl, pH 7.3) was used for measurement. The results were plotted in FIG. 16 as before target binding curves (before binding with AB-IgG).

Next, target molecules were bound to the probe molecules of the above double-stranded DNA fixed to the substrate. The binding conditions consisted of holding 50 nM of the target molecule in a buffer solution (10 mM Tris, 200 mM NaCl, pH 7.3) for one hour.

This was followed by rinsing continuously for a given length of time (here, 20 minutes) with a buffer solution (10 mM Tris, 50 mM NaCl, pH 7.3) containing no target molecules. Next, the frequency of the AC electrical field was changed in the same way as in the above-described measurement method, during which time the signals from the fluorescent label (fluorescent dye) were recorded. The results were plotted as an after target binding curve (first scan after bonding) in FIG. 16. As is apparent from FIG. 16, changes before and after target binding were observable on the high-frequency side.

In addition, after continuous rinsing for a given length of time (20 minutes) under the same conditions, similar measurements were again carried out until a total of eight measurements had been carried out. The results were each plotted as the second scan after binding to the eight scan after binding in FIG. 16.

Figure 16:
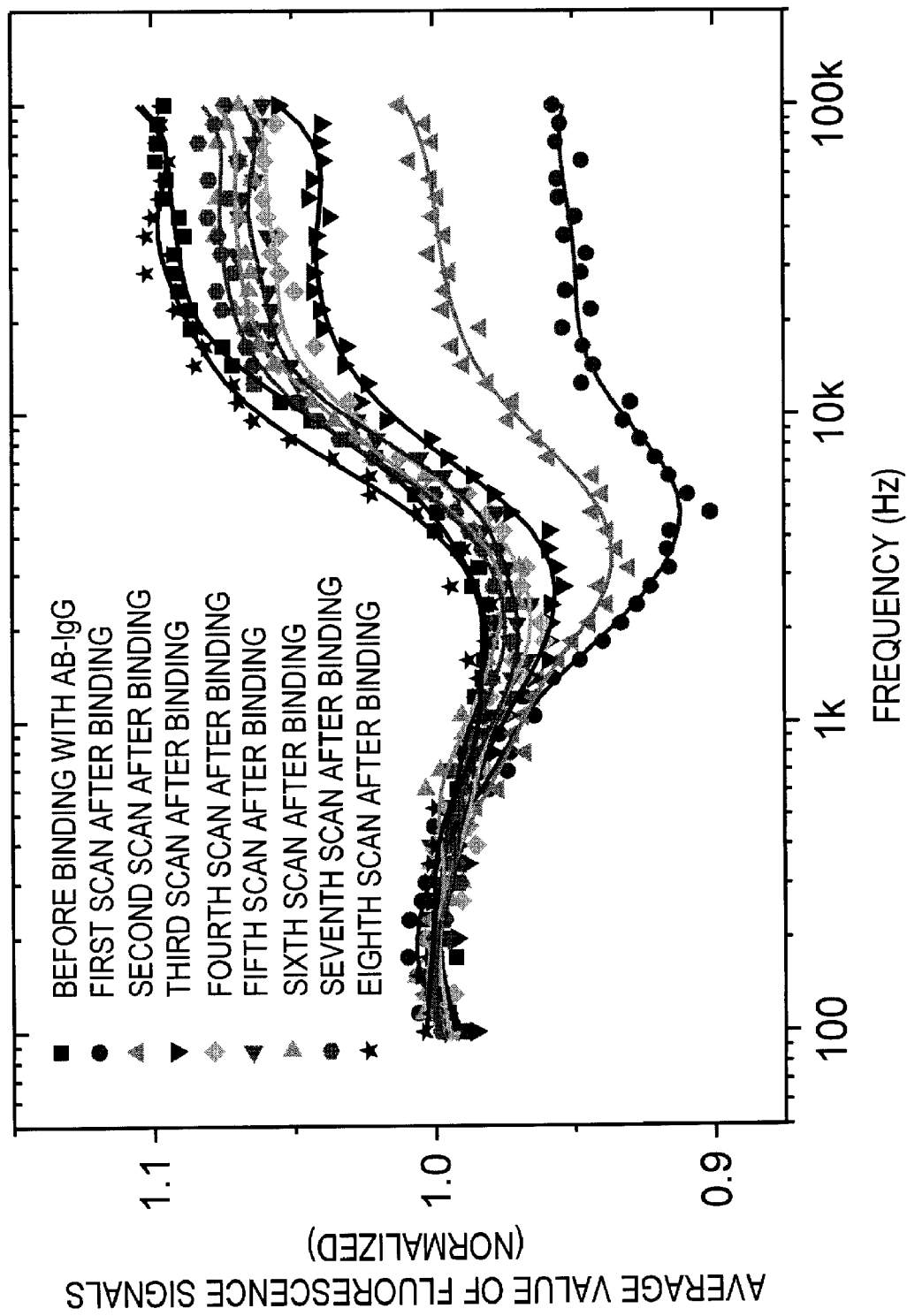
FIG. 16 is a graph showing the signal behavior of markers in response to changes in the AC voltage frequency in Example 5.
Figure 17:
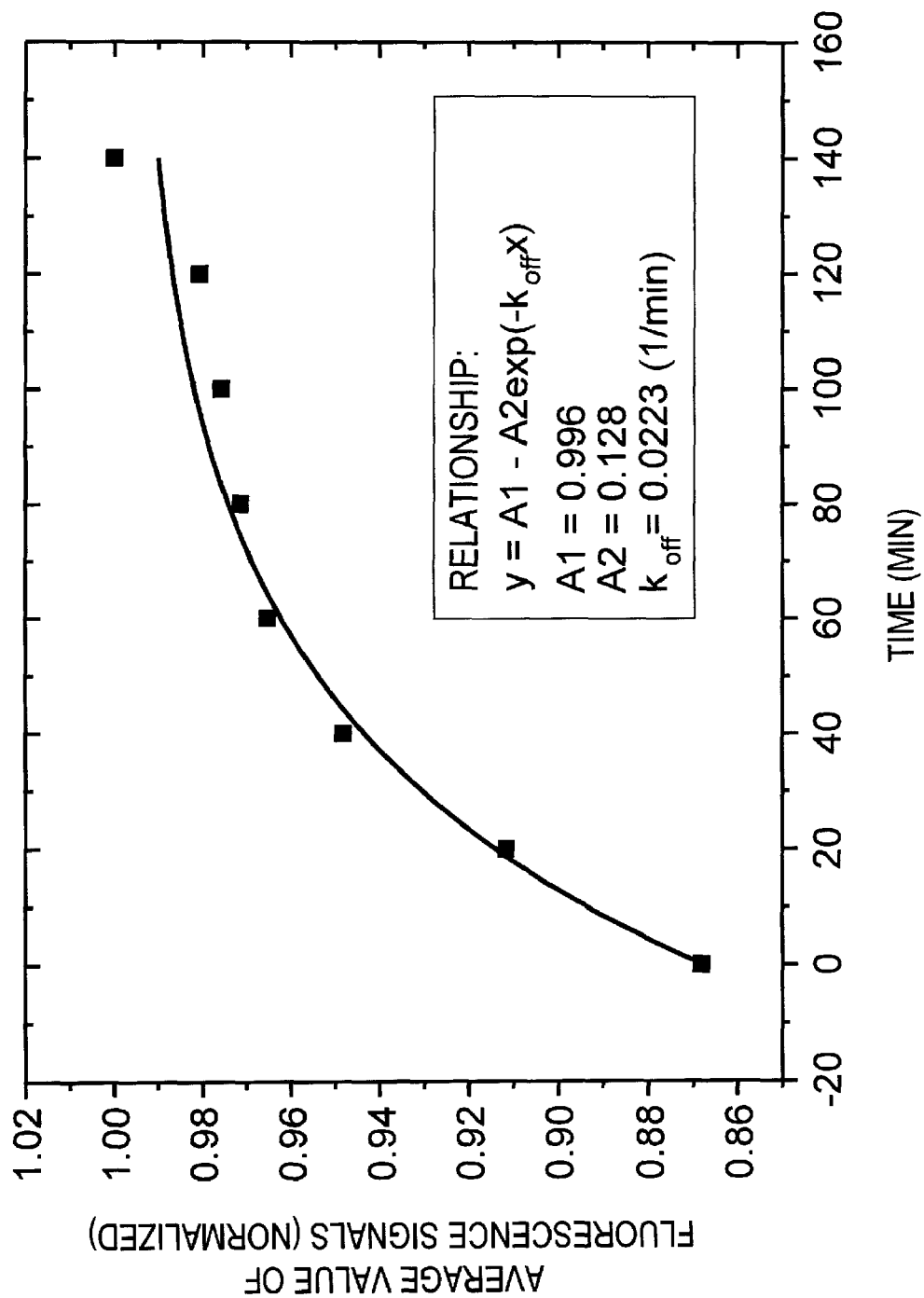
FIG. 17 is a graph showing the change over time in signals (average value) from the fluorescent labels obtained in FIG. 16.

As is apparent from FIG. 16, it can be observed that the biotin and antibiotin IgG bonds break with the passage of time, and the signals approach those prior to antibiotin IgG binding. FIG. 17 is a plot over time of the 50 kHz data on the high-frequency side in FIG. 16. The dissociation rate for biotin and antibiotin IgG can be determined from this plot. The dissociation rate constant for biotin and antibiotin IgG was 0.0223 $min^{-1}$.

The above value was obtained by continuously supplying, to the state achieved by binding a target molecule to a probe molecule having a marker, a suitable medium such as a solvent to induce the target molecule to dissociate from the probe molecule, concurrently monitoring the change over time in the average value of the signals obtained from the marker, and thereby determining the dissociate rate and dissociation rate constant between the probe molecule and the target molecule. However, by continuously supplying a target molecule to a probe molecule having a marker, inducing the target molecule to bind with the probe molecule, and concurrently monitoring the change over time in the average value of signals obtained from the marker, it is also possible to determine the binding rate and binding rate constant between the probe molecule and the target molecule.

The signals from the fluorescent label, being distinctive signals which reflect the kinetic properties of the molecules before and after binding of the target molecule, have the advantage of a high selectivity and low noise owing to the fact that, in evaluating the target, it is possible to avoid the influence of co-existing contaminants from adversely affecting evaluation and the mis-detection of nonspecifically adsorbed target.

In this example, 1 Hz signals are recorded as the average value of signals from the fluorescent label, but any frequency that is sufficiently low compared with the driving frequency may be used. Although the response of DNA to the driving frequency was closely measured from 100 Hz to 150 kHz, as is apparent from FIG. 16, evaluation of the target molecule is also possible by observing the frequencies at any two or more points where there is a significant difference.

Moreover, in the present example, the probe molecule is biotin and the target molecule is antibiotin, although anything may be used as the target, provided there is a difference between the response to the driving frequency by the probe molecule and the response by the target molecule bound to the probe molecule.

The highly selective, low-noise methods and evaluation devices for evaluating target molecules according to the foregoing aspects of the invention are highly useful in the field of nanobiotechnology, making it possible to provide evaluation methods suitable for biochips such as DNA chips and protein chips and also evaluation devices therefore.

The above aspects are especially useful for determining the Stokes radius of a target molecule, and for determining the binding rate, binding rate constant, dissociation rate and dissociation rate constant between a probe molecule and a target molecule.

What is claimed is:

1. A method for evaluating an unknown target molecule, comprising:
    providing a working electrode on a substrate and a counter electrode, probe molecules each having a marker being bound to the working electrode,
    allowing a known target molecule and the unknown target molecule to bind or not bind to the probe molecules, the known target molecule having a known Stokes radius and molecular weight,
    applying AC voltage between the working electrode provided on the substrate and the counter electrode; and
    determining signals obtained from the markers of the probe molecules when a frequency of the AC voltage is varied, and
    determining a Stokes radius or molecular weight of the unknown target molecule based on the signals obtained from the markers of the probe molecules when the frequency of the AC voltage is varied,
    wherein said determining the Stokes radius or molecular weight includes determining an association between (1) a difference between the signal obtained from the marker of the probe molecule bound to the known target molecule, at a given frequency, and the signal obtained from the marker of the probe molecule not bound to the known target molecule, at the given frequency, and (2) the Stokes radius or molecular weight of the known target molecule, and determining the Stokes radius or molecular weight of the unknown target molecule from relationship between (1) the association, and (2) the difference between the signal obtained from the marker of the probe molecule bound to the unknown target molecule and the signal obtained from the marker of the probe molecule not bound to the unknown target molecule.

2. The method for evaluating the unknown target molecule according to claim 1,
wherein the signals are an amplitude strength of a signal.

3. The method for evaluating the unknown target molecule according to claim 1,
wherein the signals are an average of multiple signals.

4. A method for evaluating a target molecule, comprising:
providing a working electrode on a substrate and a counter electrode, probe molecules each having a marker being bound to the working electrode,
allowing multiple copies of a target molecule to bind to the probe molecules,
applying AC voltage between the working electrode provided on the substrate and the counter electrode; and
determining an average of signals obtained from the markers of the probe molecules when a frequency of the AC voltage is varied, and
determining, based on the signals obtained from the markers of the probe molecules when the frequency of the AC voltage is varied, at least one of: (i) a binding rate between the probe molecules and the target molecule, (ii) a binding rate constant between the probe molecules and the target molecule, (iii) a dissociation rate between the probe molecules and the target molecule, and (iv) a dissociation rate constant between the probe molecules and the target molecule,
wherein the binding rate between the probe molecules and the target molecule or the binding rate constant between the probe molecules and the target molecule is determined by continuously supplying the target molecule to the probe molecules so as to cause the target molecule to bind to the probe molecules, during which a change over time of the average of signals obtained from the markers of the probe molecules is observed; or
wherein the dissociation rate between the probe molecules and the target molecule or the dissociation rate constant between the probe molecules and the target molecule is determined by continuously supplying a medium to a state where the target molecule is bound to the probe molecules so as to dissociate the target molecule from the probe molecules, during which the change over time of the average of signals obtained from the marker of the probe molecules is observed.

5. The method for evaluating the unknown target molecule according to claim 1, further comprising observing change over time in the average of signals obtained from the markers of the probe molecules.

6. The method for evaluating the unknown target molecule according to claim 2, further comprising observing change over time in the average of signals obtained from the markers of the probe molecules.

7. The method for evaluating the unknown target molecule according to claim 3, further comprising observing change over time in the average of signals obtained from the markers of the probe molecules.

8. The method for evaluating the target molecule according to claim 5, further comprising observing change over time in the average of signals obtained from the markers of the probe molecules.

9. The method for evaluating the unknown target molecule according to claim 1, wherein the marker is a fluorescent marker and the signal is light emission/quenching by the fluorescent marker.

10. The method for evaluating the unknown target molecule according to claim 2, wherein the marker is a fluorescent marker and the signal is light emission/quenching by the fluorescent marker.

11. The method for evaluating the unknown target molecule according to claim 3, wherein the marker is a fluorescent marker and the signal is light emission/quenching by the fluorescent marker.

12. The method for evaluating the target molecule according to claim 4, wherein the marker is a fluorescent marker and the signal is light emission/quenching by the fluorescent marker.

13. The method for evaluating the unknown target molecule according to claim 1, wherein the unknown target molecule is a protein.

14. The method for evaluating the unknown target molecule according to claim 2, wherein the unknown target molecule is a protein.

15. The method for evaluating the unknown target molecule according to claim 3, wherein the unknown target molecule is a protein.

16. The method for evaluating the target molecule according to claim 4, wherein the target molecule is a protein.

17. A method for evaluating an unknown target molecule, comprising:
providing a working electrode on a substrate and a counter electrode, probe molecules each having a marker being bound to the working electrode,
allowing at least two known target molecules and the unknown target molecule to bind to the probe molecules, each of the at least two known target molecules having a known Stokes radius and molecular weight and being different from each other,
applying AC voltage between the working electrode provided on the substrate and the counter electrode; and
determining signals obtained from the markers of the probe molecules when a frequency of the AC voltage is varied, and
determining a Stokes radius or molecular weight of the unknown target molecule, based on the signals obtained from the markers of the probe molecules when the frequency of the AC voltage is varied,
wherein said determining the Stokes radius or molecular weight includes
determining an association between (1) a difference between the signals obtained from the markers of the probe molecules bound to the at least two known target molecules, and (2) Stokes radii or molecular weights of the at least two known target molecules; and
determining the Stokes radius or molecular weight of the unknown target molecule from the relationship between (1) the association, and (2) the signal obtained from the marker of the probe molecule bound to the unknown target molecule.

18. The method for evaluating the unknown target molecule according to claim 17, wherein the signals are an amplitude strength of a signal.

19. The method for evaluating the unknown target molecule according to claim 17, wherein the signals are an average of multiple signals.

20. The method for evaluating the unknown target molecule according to claim 17, further comprising observing change over time in the average of signals obtained from the markers of the probe molecules.

21. The method for evaluating the unknown target molecule according to claim 18, further comprising observing change over time in the average of signals obtained from the markers of the probe molecules.

22. The method for evaluating the unknown target molecule according to claim 19, further comprising observing change over time in the average of signals obtained from the markers of the probe molecules.

23. The method for evaluating the unknown target molecule according to claim 17, wherein the marker is a fluorescent marker and the signal is light emission/quenching by the fluorescent marker.

24. The method for evaluating the unknown target molecule according to claim 18, wherein the marker is a fluorescent marker and the signal is light emission/quenching by the fluorescent marker.

25. The method for evaluating the unknown target molecule according to claim 19, wherein the marker is a fluorescent marker and the signal is light emission/quenching by the fluorescent marker.

26. The method for evaluating the unknown target molecule according to claim 17, wherein the unknown target molecule is a protein.

27. The method for evaluating the unknown target molecule according to claim 18, wherein the unknown target molecule is a protein.

28. The method for evaluating the unknown target molecule according to claim 19, wherein the unknown target molecule is a protein.

* * * * *